(12) United States Patent
Horiuchi et al.

(10) Patent No.: US 8,198,082 B2
(45) Date of Patent: Jun. 12, 2012

(54) METHOD OF DETERMINING CHICKEN EMBRYONIC STEM CELLS

(75) Inventors: Hiroyuki Horiuchi, Higashi-Hiroshima (JP); Haruo Matsuda, Higashi-Hiroshima (JP); Shuichi Furusawa, Higashi-Hiroshima (JP); Mikiharu Nakano, Higashi-Hiroshima (JP); Yusuke Yamashita, Kyoto (JP); Masaki Nishimoto, Higashi-Hiroshima (JP)

(73) Assignees: Hiroshima University, Hiroshima (JP); Hiroshima Industrial Promotion Organization, Hiroshima (JP)

( * ) Notice: Subject to any disclaimer, the term of this patent is extended or adjusted under 35 U.S.C. 154(b) by 185 days.

(21) Appl. No.: 12/532,548

(22) PCT Filed: Mar. 26, 2008

(86) PCT No.: PCT/JP2008/055650
§ 371 (c)(1), (2), (4) Date: Sep. 22, 2009

(87) PCT Pub. No.: WO2008/117813
PCT Pub. Date: Oct. 2, 2008

(65) Prior Publication Data
US 2010/0205684 A1 Aug. 12, 2010

(30) Foreign Application Priority Data
Mar. 28, 2007 (JP) .................................. 2007-085369

(51) Int. Cl.
*C12N 5/00* (2006.01)
*C12N 5/02* (2006.01)
*A01K 67/027* (2006.01)

(52) U.S. Cl. .......................................... 435/325; 800/19
(58) Field of Classification Search .................. 435/325; 800/19
See application file for complete search history.

(56) References Cited

U.S. PATENT DOCUMENTS

| 2003/0056241 A1 | 3/2003 | Matsuda et al. |
| 2005/0186626 A1 | 8/2005 | Matsuda et al. |
| 2008/0311654 A1 | 12/2008 | Matsuda et al. |
| 2008/0312426 A1 | 12/2008 | Matsuda et al. |
| 2009/0029458 A1 | 1/2009 | Matsuda et al. |

FOREIGN PATENT DOCUMENTS

| JP | 2008-031043 | | 2/2008 |
| WO | 00/32039 | | 6/2000 |
| WO | WO 00/32039 | * | 6/2000 |
| WO | 2004/065558 | | 8/2004 |
| WO | 2007/010287 | | 1/2007 |
| WO | WO 2007/010287 | * | 1/2007 |

OTHER PUBLICATIONS

Petitte (Mechanisms of Development, 2004, vol. 121, p. 1159-1168).*
Park (Mol. Reproduct. Dev., 2000, vol. 56, p. 475-482).*
Horiuchi (Methods Mol. Biol. 2006, vol. 329, p. 17-34).*
Canon (Dev. Dynamics, 2006, vol. 235, p. 2889-2894).*
Tsunekawa (Development, 2000, vol. 127, p. 2741-2750).*
Lavial (Development, 2007, vol. 134, p. 3549-3563).*
Nishimoto (Japanese Biochemical Society Taikai Dai 30 Kai Annual Meeting of the molecular biology society of Japan Godo Taikai Koen Yoshishu, Dec. 2007, 2P-1182).*
Alignment for Johnson, 2011.*
Alignment for Tsunekawa, 2011.*
European Search Report for corresponding European Application No. 08 72 2827 dated Feb. 14, 2011.
Nakano et al., "Establishment of novel chicken embryonic stem cells capable of differentiating into germ cells", Database Biosis [online], Biosciences Information Service, Aug. 2010, XP-002606926.
International Search Report for corresponding Application No. PCT/JP2008/055650 mailed Jun. 3, 2008.
H. Horiuchi et al., "Niwatori ni Okeru Kotai Engineering . . . ", Foods & Food Ingredients, J. Japan, 2006, vol. 211, No. 11, pp. 948-955.
N. Tsunekawa et al., "Isolation of chicken *vasa* homolog gene and tracing the origin of primordial germ cells", Development, 2000, vol. 127, pp. 2741-2750.
T. Teramura et al., "Derivation of Presumptive Gonocytes in Vitro from Primate Embryonic Stem Cells", Reproduction, Fertility and Development 2007, vol. 19, No. 1, p. 231.
M. Nishimoto et al., "Shinki Niwatori . . . ", Dai 80 Kai The Japanese Biochemical Society Taikai Dai 30 Kai Annual Meeting of the Molecular Biology Society of Japan Godo Taikai Koen Yoshishu, 2007, 12, 2P-1182.
H. Horiuchi et al., "Transgenic Niwatori . . . ", BRAIN techno news, Mar. 15, 2002, vol. 90, Sosetsu 1-4.
J.N. Petitte et al., "Avian pluripotent stem cells", Mechanisms of Development, 2004, vol. 121, pp. 1159-1168.
T.S. Park et al., "Derivation and Characterization of Pluripotent Embryonic Germ Cells in Chicken", Molecular Reproduction and Development, 2000, vol. 56, pp. 475-482.
H. Horiuchi et al., "Maintenance of Chicken Embryonic Stem Cells in Vitro", Methods in Molecular Biology, vol. 329, pp. 17-34, 2006.
S. Canon et al., "Germ Cell Restricted Expression of Chick Nanog", Developmental Dynamics, vol. 235, pp. 2889-2894, 2006.

(Continued)

*Primary Examiner* — Michael C. Wilson
(74) *Attorney, Agent, or Firm* — Renner, Otto, Boisselle & Sklar, LLP

(57) ABSTRACT

A chicken embryonic stem cell is established, which stably has pluripotency and an ability of being differentiated into a germ cell. For evaluating on whether or not the chicken embryonic stem cell can be applied to genetic modification technique, detection is made on a protein which serves as an indicator of the ability of being differentiated into a germ cell. This provides (i) a chicken embryonic stem cell applicable to genetic modification technique and (ii) a method for evaluation of the chicken embryonic stem cell.

3 Claims, 16 Drawing Sheets

OTHER PUBLICATIONS

B. Pain et al., "Long-term in vitro culture and characterisation of avian embryonic stem cells with multiple morphogenetic potentialities", Development, 122 (8), pp. 2339-2348, 1996.

van de Lavoir et al., "High-grade transgenic somatic chimeras from chicken embryonic stem cells", Mechanisms of Development, vol. 123 (1), pp. 31-41, 2006.

van de Lavoir et al., "Avian Embryonic Stem Cells", Methods in Enzymology, vol. 418, pp. 38-64, 2006.

H. Horiuchi et al., "Chicken Leukemia Inhibitory Factor Maintains Chicken Embyronic Stem Cells in the Undifferentiated State", The Journal of Biological Chemistry, Vo. 279, No. 23, pp. 24514-24520, 2004.

Y. Yamashita et al., "Effect of novel monoclonal antibodies on LIF-induced signaling in chicken blastodermal cells", Development & Comparative Immunology, vol. 30(5), pp. 513-522, 2006.

K. Mitsui et al., "The Homeoprotein Nanog is Required for Maintenance of Pluripotency in Mouse Epiblast and ES Cells", Cell, vol. 113(5), pp. 631-642, 2003.

I. Chambers et al., "Functional Expression Cloning of Nanog, a Pluripotency Sustaining Factor in Embryonic Stem Cells", Cell, vol. 113(5), pp. 643-655, 2003.

van de Lavoir et al., "Germline transmission of genetically modified primordial germ cells", Nature, vol. 441, pp. 766-769, 2006.

Form PCT/IPEA/409 for corresponding Application No. PCT/JP2008/055650.

* cited by examiner

F I G. 1
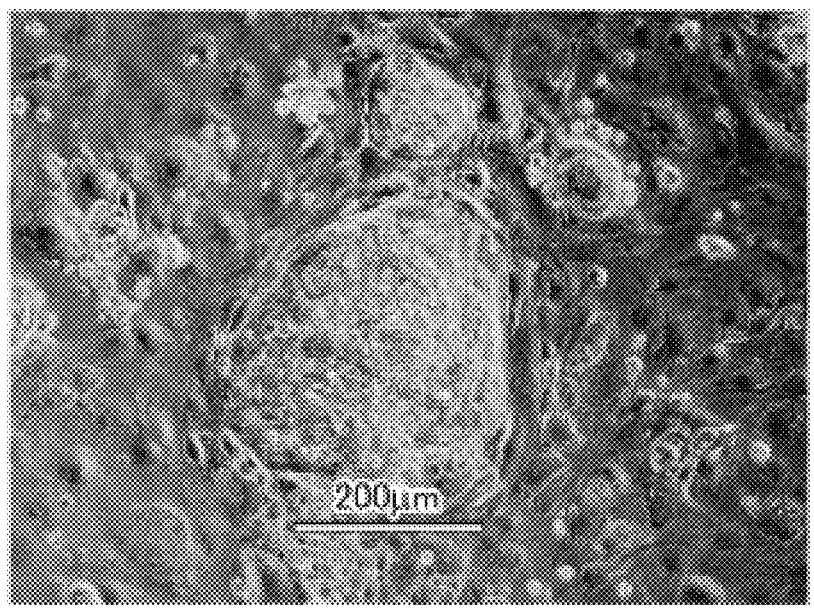

FIG. 2
(a)
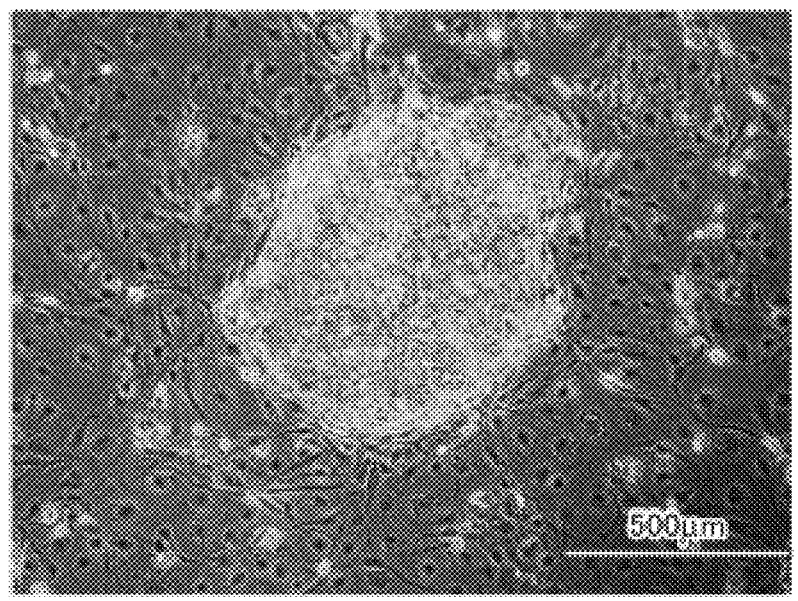
(b)
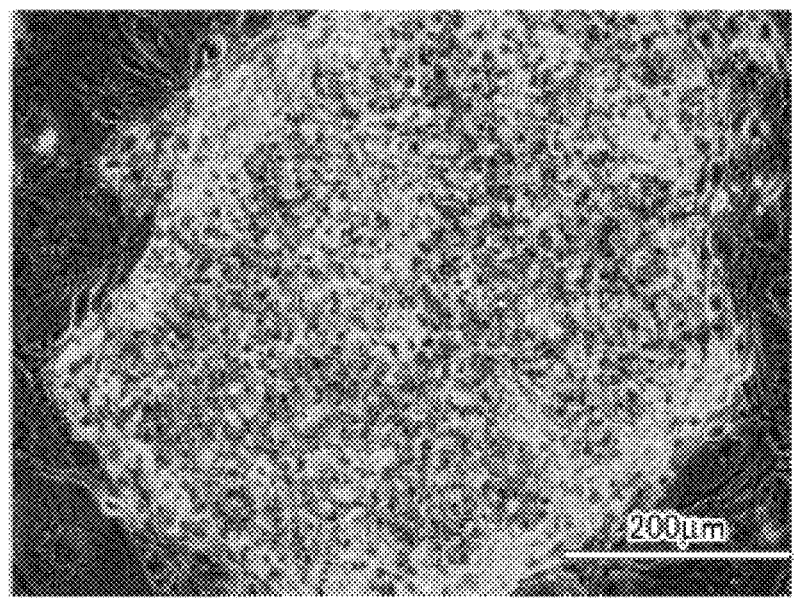

F I G. 3
(a)
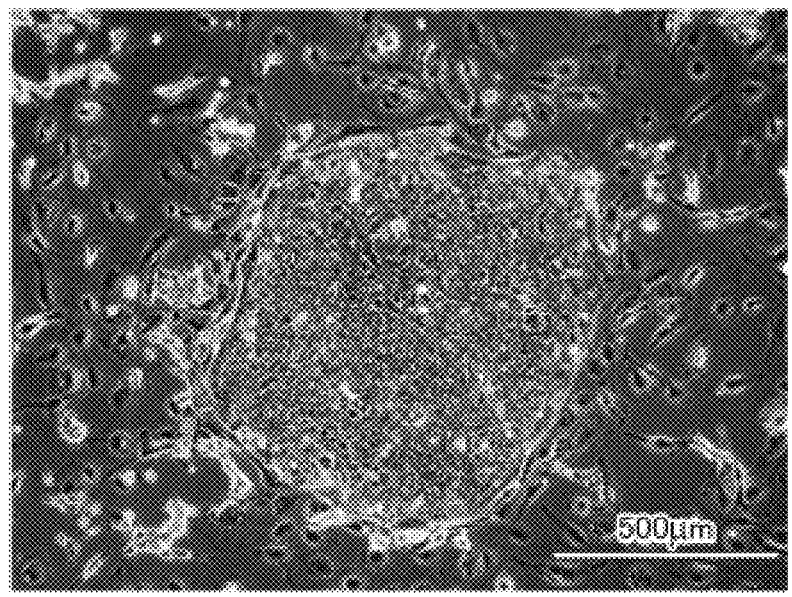
(b)
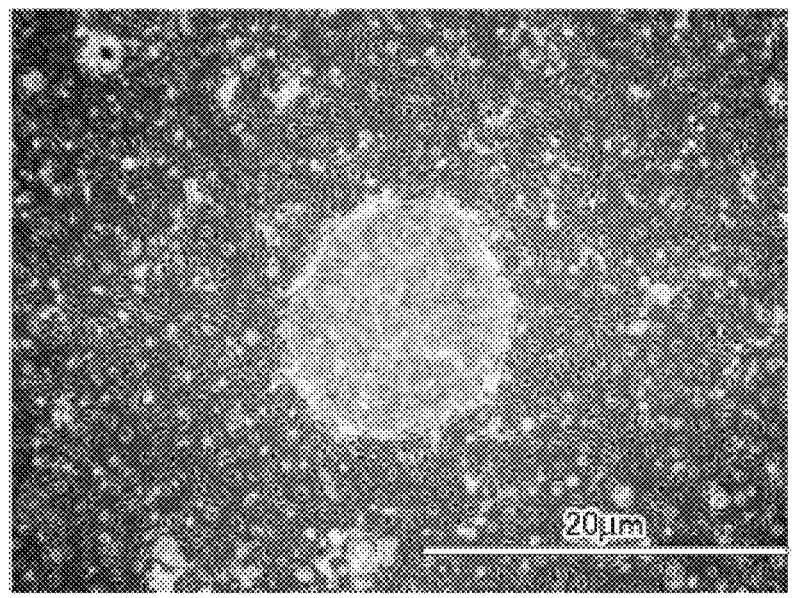

```
Human    MSVDPACPQSLP-CFEASDCKESSPKPVICGPEEHYPSLQKS-SABMPETETVSPLDSSM  58
Mouse    MSVGLPGPRSLPSSEEASHSGHASSNPAVTHP-EBYSCLQGS-ATBMLCTEAASSRPSSB  58
Chicken  MSAHLAMPSYGSVRCGHYTWPSPGSMDSASAAEAPAADLSLTTBQKTPCHPDASPASSSS  69
           *  *         *        *   *        *  *       *    **  **

Human    DLLIQDSPDSSTSPKGKQPTS-AENSVAKKEDKVPVKQKTRTVFSSTQLCVLKDRFQKQ  117
Mouse    DLPLQGSPDSSTSPKQKLSSPEADKGPEEEENKVLARKQKNRTVFSQRQLCALKDRFQKQ  118
Chicken  GTLIQYTPDSATSPTADHPSHRPTFQKVKDKGRSGTKKAKSRTAFSQRQLQTLHQRFQSQ  120
           * *  ****.***  .  *        *  *  *  *  ** ** ** ** * ****

Human    KYLSLQQMQELSHILNLSYKQVKTWFQHQRMKSKRWQK-SNWPKNSNGVTQKASAP-TYP  175
Mouse    KYLSLQQMQELSSILNLSYKQVKTWFQHQRVKCKRWQK-NQWLKTSNGLIQKGSAPVEYP  177
Chicken  KYLSPHQIRELAAALGLTYKQVKTWFQHQRNKFKRCQKESQNVDKGIYLPQHGPHQAAYL  180
         ****  *  **  *    ** *************  ** ** *        *    *

Human    SLYSSYHQGCLVNPTGHLPMNSHQTWNHSTMS-----NQTQHIQSNSHSNNTQTWCTQS  230
Mouse    SIHCSYPQGYLVRASGSLSMNGSQTWTHPTMSSQTWTRPTMRNQTWTHPTWSSQANTRQS  237
Chicken  DWTPTFHQGFPVVANRHLQAVTSAHQAYSSGQ------TYGNGQGLYPPRAVEDEGPPG  233
           *  ** *    *  *  *        *           *    *   *

Human    NHHQAMN-SPFYBCGEHSLQSCHQPQFHGPASDLBAALEAACBGLNVIQQTTRYPSTFQT  289
Mouse    NHGQPMHAAPLHNFGEDFLQPYVQLQQHFSASDLBVELEAT------RESHAHFSTPQA  290
Chicken  KSGTSCNTQQANGLLSQQMNFYHGYSTHVDYDSLQAHDTYS---PQSTSDSITQFSSSPV  290
             *      *   *    *    **                    *     **

Human    MDLFLHYSMSMQPEDV---  305
Mouse    LELFLHYSVTP-PGEI---  305
Chicken  RHQYQAPNNTLSTQHGYET 309
           *    *     *
```

(b)

| | Chicken | Human | Mouse |
|---|---|---|---|
| Chicken | | 24.3 (65.0) | 24.6 (65.0) |
| Human | 65.1 (90.0) | | 59.1 (85.0) |
| Mouse | 63.9 (90.0) | 89.9 (96.7) | | similarity (%) → identity (%)

F I G. 6
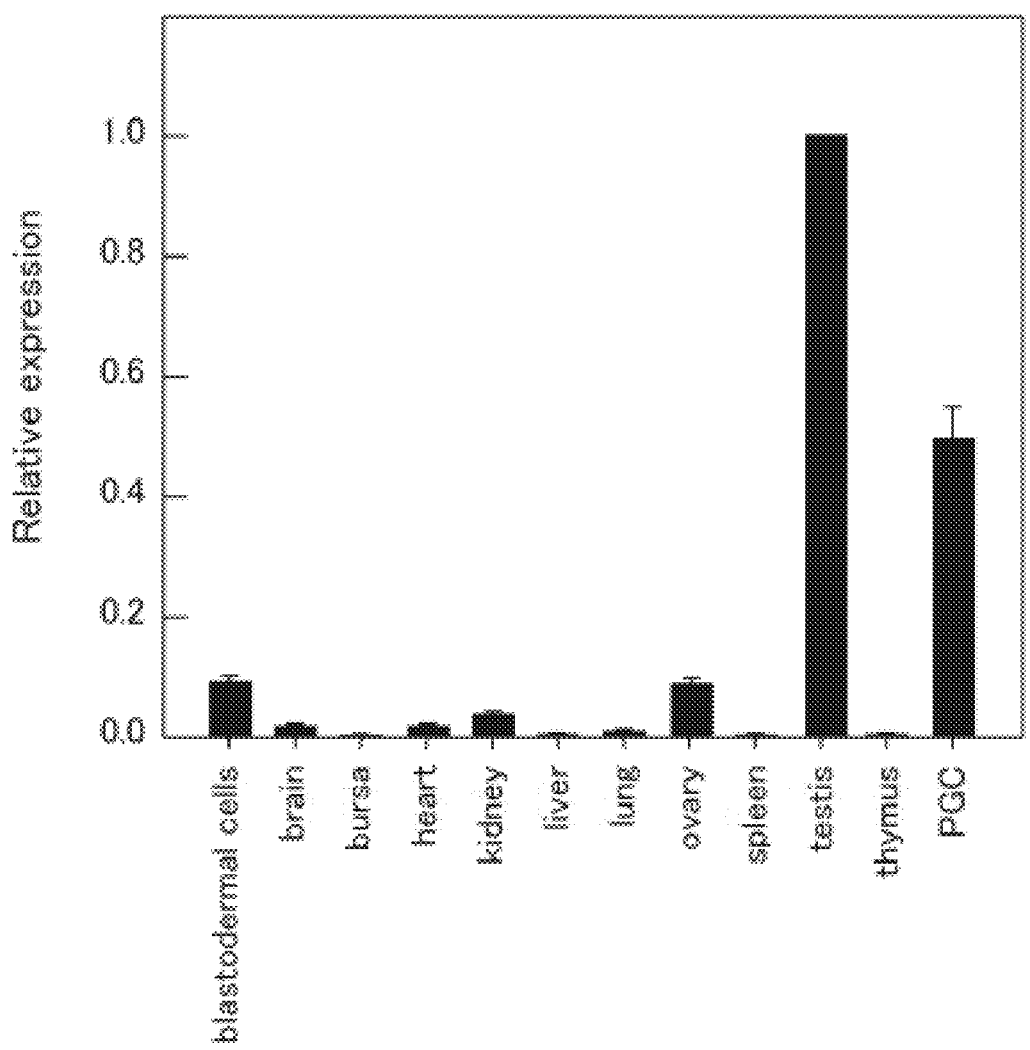

FIG. 7
(a)
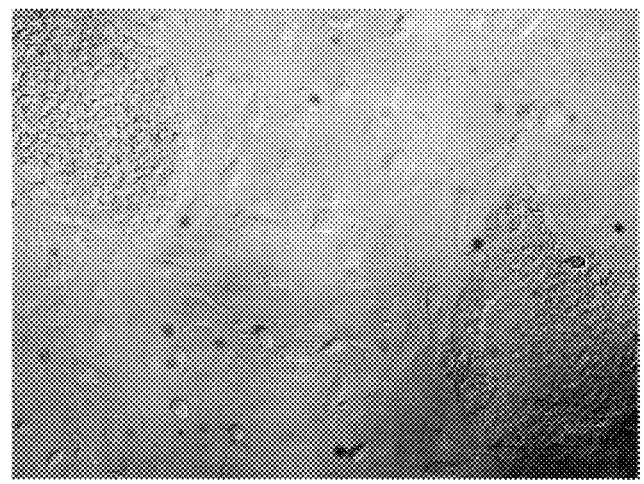
(b)
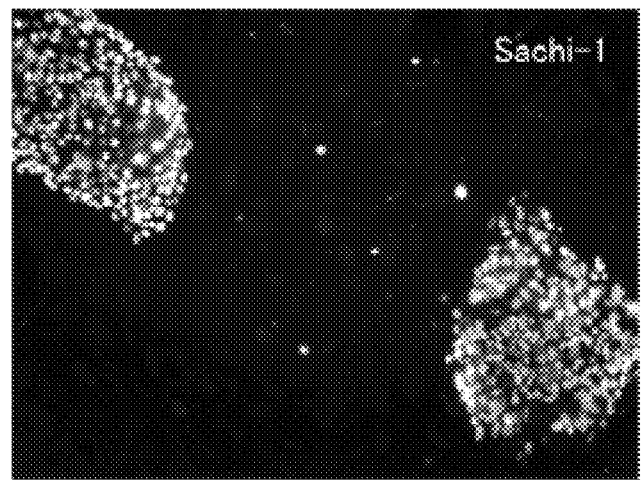
(c)
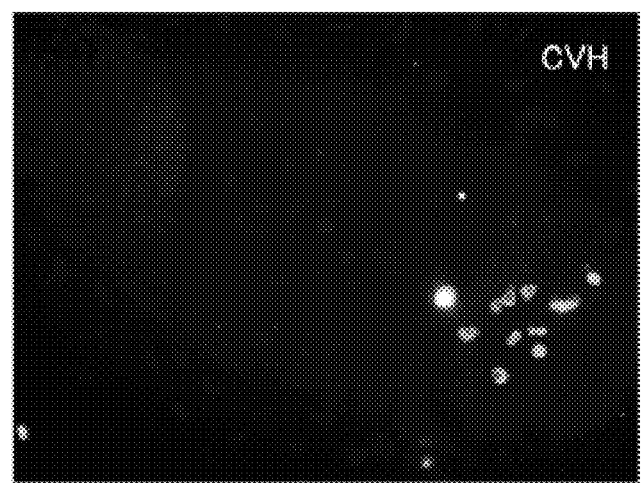

FIG. 8
(a)
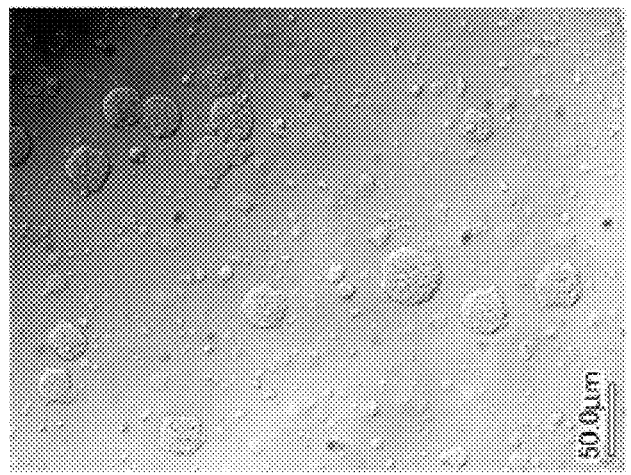
(b)
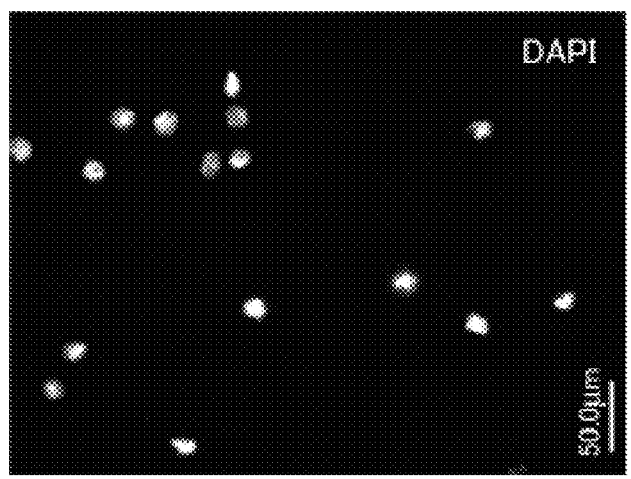
(c)
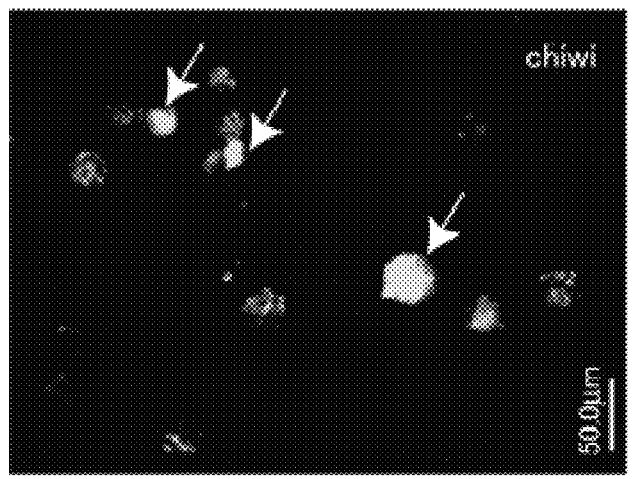

FIG. 10
(a) anti-chiwi antibody
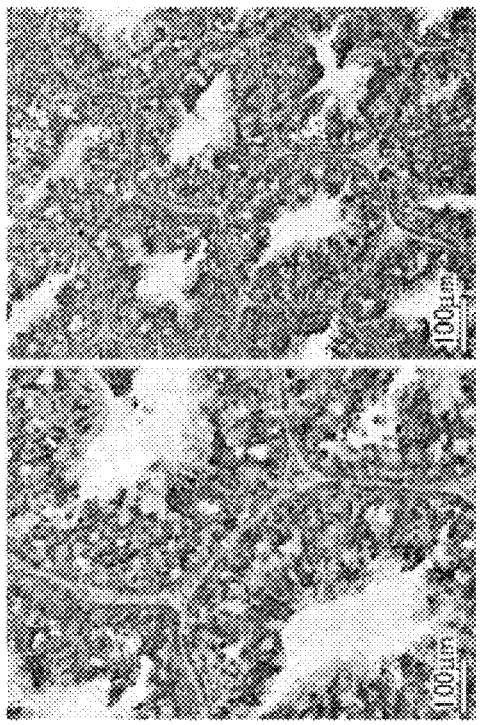
(b) anti-CVH antibody
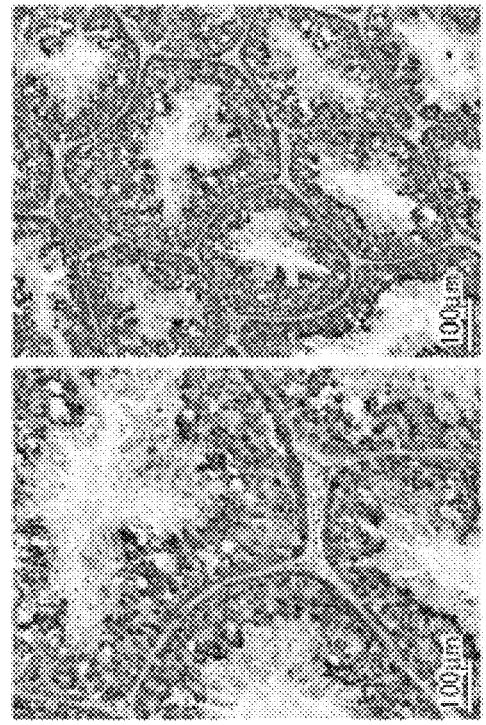

F I G. 1 2
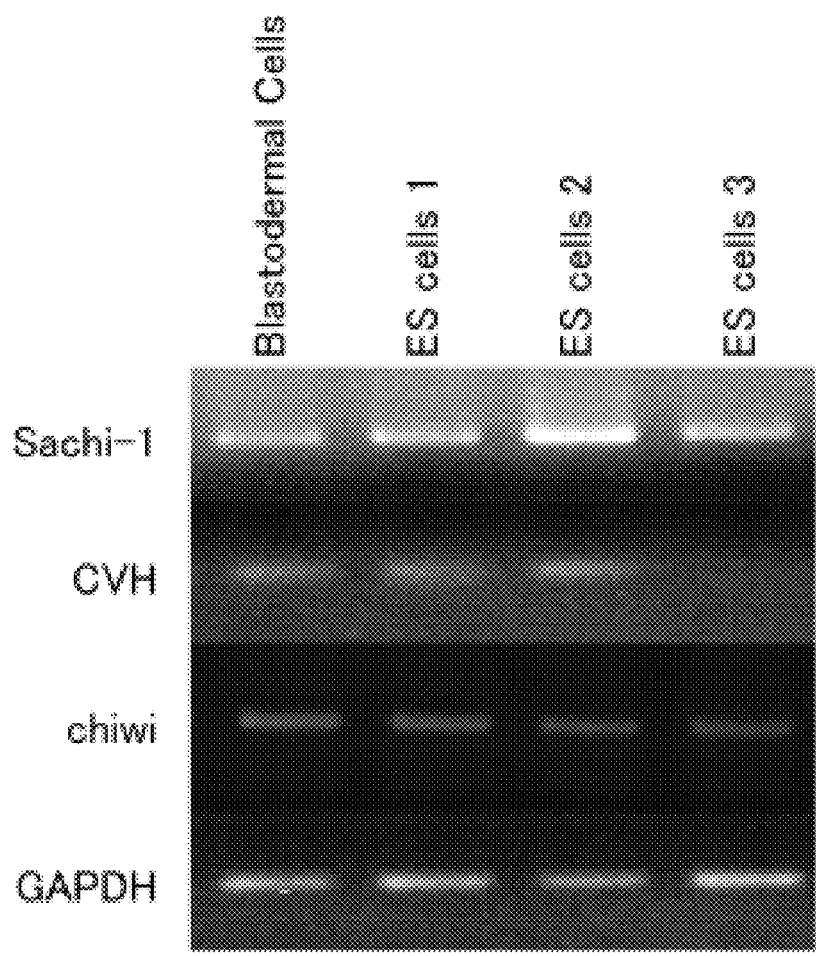

FIG. 13
(a)
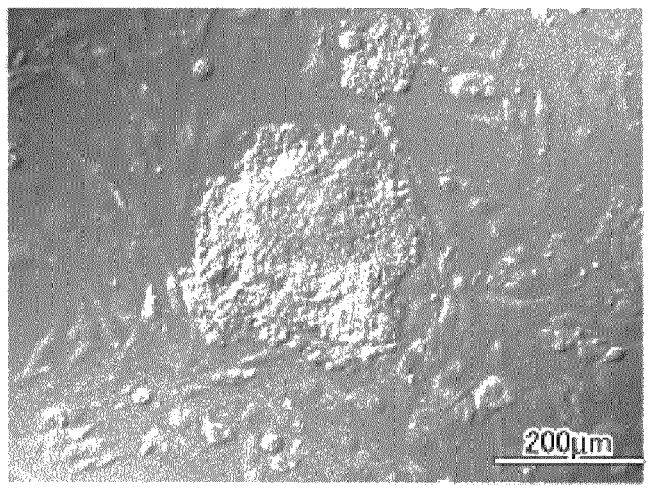
(b)
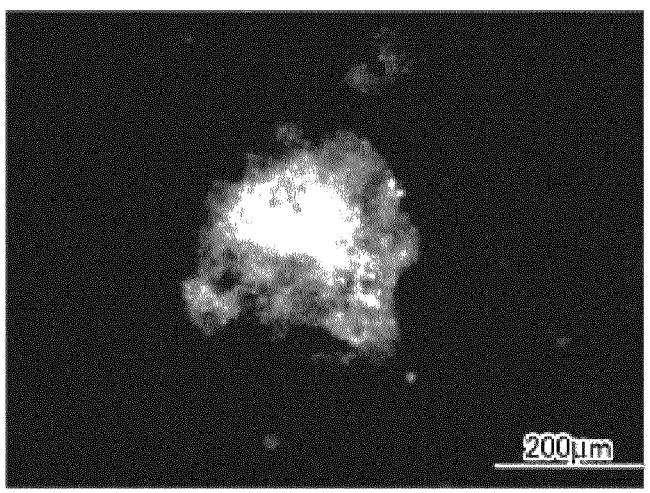
(c)
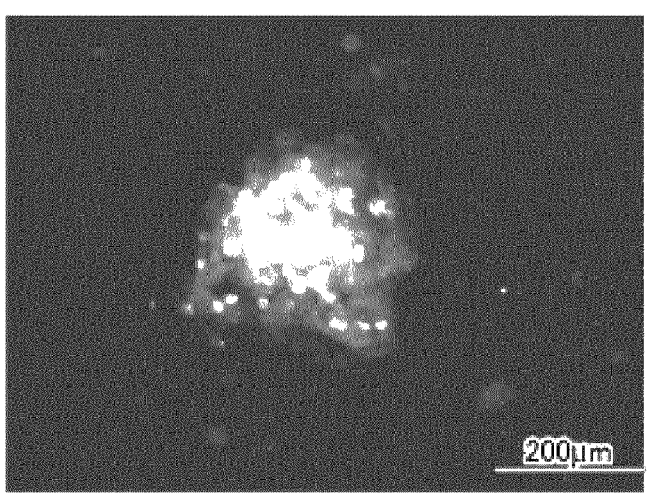

F I G. 14
(a)
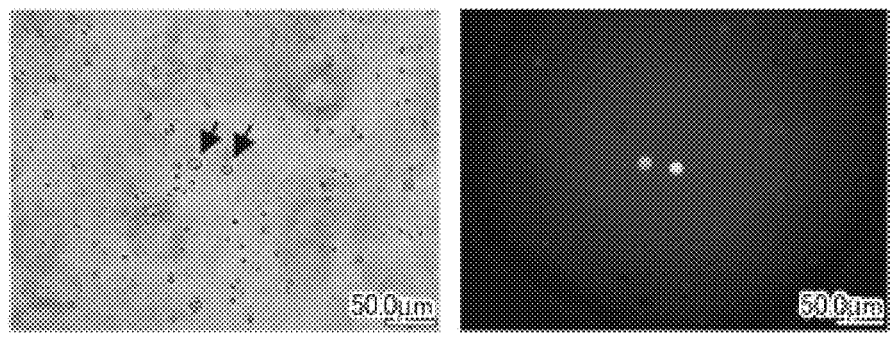
(b)
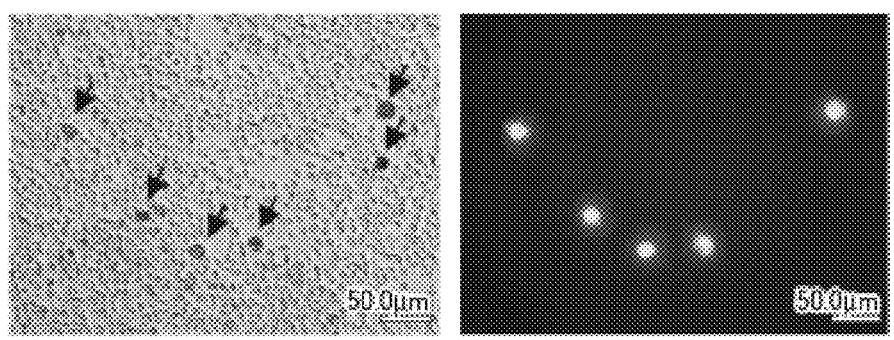

FIG. 15
(a)
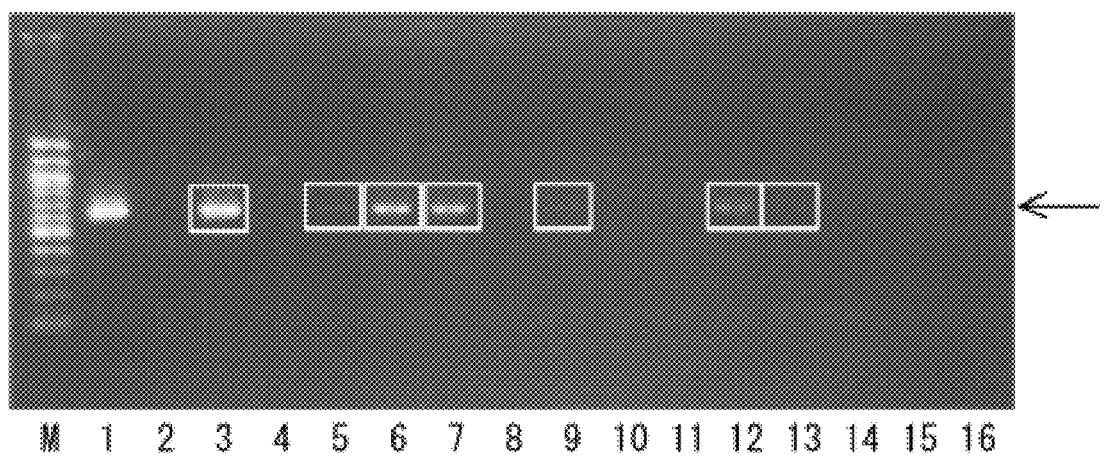
M 1 2 3 4 5 6 7 8 9 10 11 12 13 14 15 16
(b)
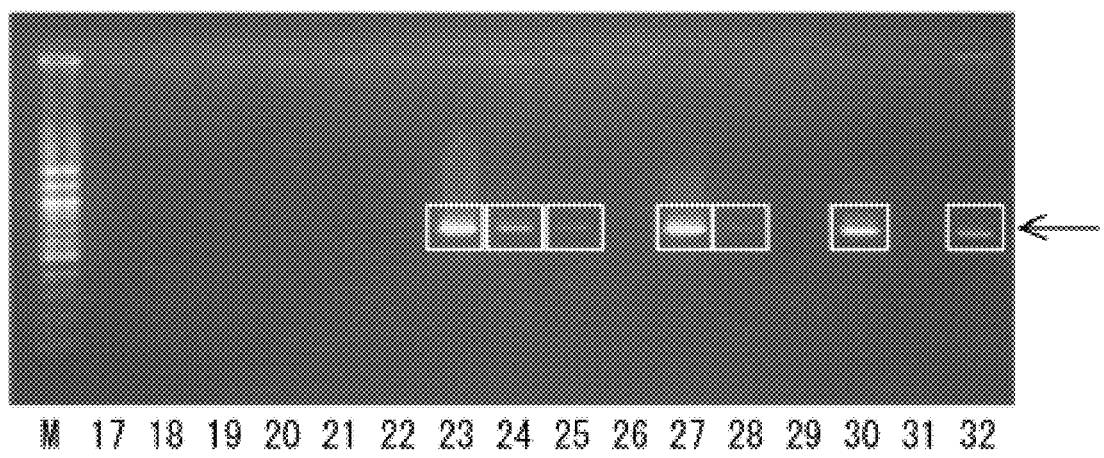
M 17 18 19 20 21 22 23 24 25 26 27 28 29 30 31 32

FIG. 16
(a)
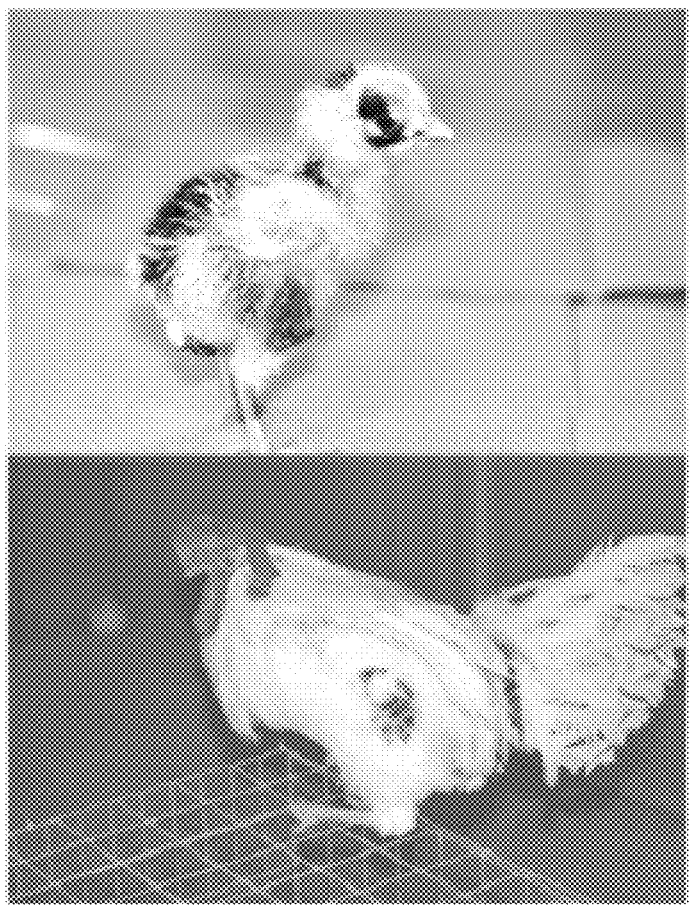
(b)

SEQUENCE LISTING

```
<160> NUMBER OF SEQ ID NOS: 20

<210> SEQ ID NO 1
<211> LENGTH: 3130
<212> TYPE: DNA
<213> ORGANISM: Gallus gallus domesticus

<400> SEQUENCE: 1
gggtctctgg gctcccctc cattctttgt acttgggtgg ggaccgatga ggaggcgtag      60
gtgggtagca agactgttaa atgtgagggc gggggtgcca gcccagcccg ccgcacggga     120
```

```
cggccttgct cacacctgct aggcctgagg tggaaacaag gcccctcct cccagccccg      180 gggggtcggg tgtgcgggca gcaaagaact gactcccacc gaggaaccaa aggggggaagc    240 tggccttgct gtcctagtcc tcccccactc tccgaatatc cccatagcca ctcccctcca    300
atcaactgac ttttaacatg ataatggtcg tgacaatctc ttggctaaag ccagtctggg    360
gaggacataa aacattgccc ctcaccgcct aatggggtat ctccgtgcag taggcgcgta    420
tgcaaccagc tcaccgccag caacggctgg aggtgctgtc ccgaccatga gcgctcacct    480
ggccatgccg tcctacggct ctgttaggtg cggacactac tactggccct ctccgggcag    540
catggatagc gcgtctgccg cggaagctcc agcagcagac ctctccttga ccacagagca    600
gaaaacgccc tgccacccag atgcctctcc agcttcttcc agctctggga cactcattca    660
gtatacccca gactctgcca ctagccctac tgcagaccac ccatctcacc gccccacttt    720
tcagaaggtt aaggataaag gtgagagtgg gacaaggaag gccaagagcc gcacagcttt    780
ctcccaggag cagctgcaga ccctgcacca gcggtttcag agccagaagt acctcagccc    840
ccatcagatc cgggagctgg ctgctgctct ggggctcacc tacaagcagg tgaagacgtg    900
gtttcagaac caacgaatga agtttaaacg ttgccagaaa gagagtcagt gggtggataa    960
agggatttat ctaccacaga atgggtttca tcaagctgcg tatctggata tgaccccac    1020 atttcaccag ggcttccctg ttgttgccaa cagaaacctt caggctgtga ccagtgcaca    1080
ccaggcttac agcagtggcc agacttatgg gaatgggcag ggcctgtatc cgttcatggc    1140
tgtggaggat gagggcttct ttggaaaagg tggaacaagc tgcaacaccc agcaggccat    1200
gggtttatta agtcaacaga tgaacttcta tcatggctac tctaccaatg tggattacga    1260
cagcttgcag gcagaagata cctacagctt ccagagcacc tctgatagta tcacacagtt    1320
ctcgagctct cctgtacggc atcagtacca ggccccttgg catacccgg ggacccagaa     1380 tggttatgag acttagacct aagtattgtt ctttcccttc ctcctgtttt gtctcatggg    1440
gtttctaggg tcttgactca tagatccaat ttctattcct ttcttttgcc cctccttctc    1500
aattcctgct ttaactgttg gtggggtcta gcaccctgct atttcaggtt tcttttctct    1560
ttaaaggcat ctctgtgcat agctaaccct ttgcaagggt gttctgtgtg tagacaggtg    1620
aaattgcatt tatggagggg aatgtgcaat gccacagtca ggagcagcag agatggcgaa    1680
gatccatgtt tactgtccaa gacccactcc gctgcctctt ttgcggatga ttctctgatc    1740
ttcaccatgt gtcttgcagc caaaacttag agaaaacttt taatttctgc aagaaatacc    1800
ctatttgtag cccagagtct ttcctgctgt cttgccttt tctgctgtga cctcagtcat     1860
ctagtaaatt catctgggtc ctttaaatct ctgaactgaa agcctaaata tcatcttatc    1920
ttggatggtt tgatccagtt actctgtctt tccacctgga gaggtcagta cctgcctacc    1980 cttttgtctcc tgccttcctg tgttcgtaag gctgtttaaa gaacaggagg agaaaagaga  2040
agttggagag aatgttgtct gtacctgatg tggaaatgtt taaaacgatt tccaaagctg    2100
atggatgctt tgtgtctgtc aaataactga cgatcaatct ctggaactat ttgtaacaat    2160
ttaaatcttg tcttccttaa tctctctgct gagaaaatga tagcttgtcc caatctgaat    2220
attgcagcag atggtacacc aaaatgccat tgctggaaat gtgagtagtg ctatattta    2280 gccatcttct gagtgttgag aaatagtttg cttatctgta tatcaggatt cactagcaat    2340
ttgtgaacac agtgtcaata catgggcagc tttctcagag gtagagagta cgcaaaggta    2400
aagggccttt ttacattaaa gattgtttca tggttagtta ttctgaaacc tgaatgtcag    2460
ggaggaaaac cctgttggat agtagtggag ttggcatcca aggggctaga gcaggatgtt    2520
```

```
tccctaatct cttgtctaat ctcagtttta agatagcaag ctaatgtttt tatcccatct    2580
ccagtgctta gttggatctt ttccatattc tcctgctgaa aggtatacca gctacctctt    2640
ggggtagcca ttctggagga gatggcaagt tcagagaaac ctagatagac aatcagagga    2700
tgaaaatggc aattaatgtt ttgattttct ttttcaaaag aactgaatca tcccttt cag   2760 gatggagatt actagaagtc agcaactgcc tttgcaaaac tggatcttta agtagtgaga    2820
ttggagagtc cagtctgcca ctgcccaaga atacacaatg tcttgagctg caagagcaa     2880 ataaatgata aaagcataaa taattttttt cactaatgtg cagtttgtgc tgtaattctg    2940
tattttaatg tatgtgcaag gattatgtgt cacagttgag ctttcactac aaagatggat    3000
gcttgctgct gttctcgcag tgatcatggc catgttttat ggcatacatg tgttgtctac    3060
tgctttactt ctgcttgatg tttatataga ctcgcttgaa ttgaaaataa atgactttat    3120
tttaatgctg                                                            3130
```

<210> SEQ ID NO 2
<211> LENGTH: 309
<212> TYPE: PRT
<213> ORGANISM: Gallus gallus domesticus

<400> SEQUENCE: 2

```
Met Ser Ala His Leu Ala Met Pro Ser Tyr Gly Ser Val Arg Cys Gly
  1               5                  10                  15

His Tyr Tyr Trp Pro Ser Pro Gly Ser Met Asp Ser Ala Ser Ala Ala
                 20                  25                  30

Glu Ala Pro Ala Ala Asp Leu Ser Leu Thr Thr Glu Gln Lys Thr Pro
             35                  40                  45

Cys His Pro Asp Ala Ser Pro Ala Ser Ser Ser Gly Thr Leu Ile
         50                  55                  60

Gln Tyr Thr Pro Asp Ser Ala Thr Ser Pro Thr Ala Asp His Pro Ser
 65                  70                  75                  80

His Arg Pro Thr Phe Gln Lys Val Lys Asp Lys Gly Glu Ser Gly Thr
                 85                  90                  95

Arg Lys Ala Lys Ser Arg Thr Ala Phe Ser Gln Glu Gln Leu Gln Thr
            100                 105                 110

Leu His Gln Arg Phe Gln Ser Gln Lys Tyr Leu Ser Pro His Gln Ile
        115                 120                 125

Arg Glu Leu Ala Ala Ala Leu Gly Leu Thr Tyr Lys Gln Val Lys Thr
    130                 135                 140

Trp Phe Gln Asn Gln Arg Met Lys Phe Lys Arg Cys Gln Lys Glu Ser
145                 150                 155                 160

Gln Trp Val Asp Lys Gly Ile Tyr Leu Pro Gln Asn Gly Phe His Gln
                165                 170                 175

Ala Ala Tyr Leu Asp Met Thr Pro Thr Phe His Gln Gly Phe Pro Val
            180                 185                 190

Val Ala Asn Arg Asn Leu Gln Ala Val Thr Ser Ala His Gln Ala Tyr
        195                 200                 205

Ser Ser Gly Gln Thr Tyr Gly Asn Gly Gln Gly Leu Tyr Pro Phe Met
    210                 215                 220

Ala Val Glu Asp Glu Gly Phe Phe Gly Lys Gly Thr Ser Cys Asn
225                 230                 235                 240

Thr Gln Gln Ala Met Gly Leu Leu Ser Gln Gln Met Asn Phe Tyr His
                245                 250                 255

Gly Tyr Ser Thr Asn Val Asp Tyr Asp Ser Leu Gln Ala Glu Asp Thr
```

-continued

```
                260                 265                 270
Tyr Ser Phe Gln Ser Thr Ser Asp Ser Ile Thr Gln Phe Ser Ser Ser
        275                 280                 285

Pro Val Arg His Gln Tyr Gln Ala Pro Trp His Thr Leu Gly Thr Gln
        290                 295                 300

Asn Gly Tyr Glu Thr
305
```

<210> SEQ ID NO 3
<211> LENGTH: 3363
<212> TYPE: DNA
<213> ORGANISM: Gallus gallus domesticus

<400> SEQUENCE: 3

| | | | | | |
|---|---|---|---|---|---|
| ggtgtctgtg | tgctacaaat | aaagcgtttg | ctgctccgct | gataatgtag | tgaattagtc | 60 |
| gggattgtgt | tggtaagtgt | cacttcaaag | tggcgttggt | gggctcagag | tttgaagttc | 120 |
| ctgccatgct | ctccggtgca | gctgttttc | ttcacagctt | gagaatgcct | gggctgcgct | 180 |
| gttaggcttc | agcttggctg | taaggagctg | ttaattaccc | acactggatg | gcaaatgaa | 240 |
| acagtgcttc | ttgtaacacg | tttgagtaag | gatgggggaa | gcagaagact | gagcactaat | 300 |
| gctgtgggtg | ctttgtcttc | aaagggaaca | tgacaggaag | agctagagcc | agagcgagag | 360 |
| ggagacctcc | aggacaggag | gctgccattc | ctcctgtggg | agctgcatct | gctcaaaaga | 420 |
| ctttgccaag | tcatccatct | gaacagcggc | aatctctgca | gccatgtcat | cctccaccac | 480 |
| tgacagaaga | acctggtggc | cgtgggcgac | agagaggccc | tcaggatgct | ccaaagacac | 540 |
| taggattaca | gatttcagca | gggtttcagg | aactgtcttt | agcagatagg | ggcggacgtc | 600 |
| gtcgggattt | ccatgacctc | ggggtaaata | ctcgacaagc | catagaacac | gttagagaat | 660 |
| caaaaactgg | ctcttcaggt | gctatgataa | aattaattgc | aaatttttt | cgtctcacat | 720 |
| ctcgacccca | atgggcttta | tatcaatacc | atgtagacta | taatcctgag | atggaagcac | 780 |
| gccgccttcg | atcaggtttg | ctctttcagc | atgaagacct | aattggaaaa | acgcatgcat | 840 |
| ttgatggatc | aatattattc | ttgccaaaaa | gactgccaaa | taaggttact | gaagtatatt | 900 |
| ctaagacccg | aaatggagaa | gatgtgagga | tcacgatcac | attgactaat | gaattaccac | 960 |
| ctacttcacc | tacatgtctg | cagttttaca | acatcatttt | tagaaggctt | ctgaagatga | 1020 |
| tgaattttca | gcaaattgga | cgtaactatt | acaaccctaa | ggacccagtc | agcatcccta | 1080 |
| atcacaggtt | gatggtttgg | ccaggcttca | caagttctat | tctccagtat | gaggagagca | 1140 |
| ttatgttatg | tgcagatgtg | agccataaga | ttcttcgtag | tgaaacagtt | ttggatttta | 1200 |
| tgtacagtct | ctatgaacag | gttgaagaga | aagatttag | agatgcctgt | gcaaaggagc | 1260 |
| tgataggtgt | aattgttctt | acgaagtaca | ataacagaac | atacagagtt | gatgacatcg | 1320 |
| actgggatgc | caatccacag | tgtactttta | gacgagcaga | tggctctgaa | atcagctata | 1380 |
| tagactacta | caaaaggcaa | tataaccaag | atatcagtga | cttgaaccag | cctgtcttga | 1440 |
| tcagtcagta | tcggaggaag | agaggaaatg | tgacggtagg | acctgtggtt | ctaatcccag | 1500 |
| agctgtgcta | cctaacagga | ttaactgaga | agatgaggaa | tgattttaac | atgatgaaag | 1560 |
| acttggctgt | tcatacacga | ctttcacctg | agcaaagaca | acgtgaaatt | ggaaagcttg | 1620 |
| ttgactgcat | gaaaaagat | gaatgtgttc | agaaggaact | ccgggactgg | ggtttaagct | 1680 |
| ttgattctag | cttactgtcc | tttacgggaa | gagttgttca | agcagaaaag | atccttcaag | 1740 |
| caggaaatgt | gtttgattac | aatcctcagt | ttgctgattg | gtcacgggaa | accagggtag | 1800 |
| ctcccttaat | ccatgcaaag | cctttggaca | actggttact | gatatacaca | cggcgcaact | 1860 |

```
atgatgctgc taatatgtta cttcagaatc tgtttaaagt cacaccatct atgggaatca      1920
gaatgaacaa ggcaaccatg attgaagtgg atgatagaac agaagcttat ttaagggttt      1980
tgcaacaaag tattactccg acacaaaca tagtagtttg tattttgtct agtacccgaa       2040
aggataagta tgatgctatc aagaaatacc tatgtacgga ttgtcccatt ccaagtcagt      2100
gcgtggttgc tcgtacttta agcaagcctc agactgctct ggccatagtg acaaaaattg      2160
ccttgcagat gaactgtaaa atgggtggag aactctggag tgttgagatc cctctgaagc      2220
agttaatgat tgtgggcatt gattgttacc atgatacttt atctggaaag cagtcaattg      2280
ctggatttgt ggctagcctg aatgaaaaaa tgacacggtg gttttcacgc tgcgttgttc      2340
aaagccgtgg gcaggaaatt gtggatgggc tcaaagcctg cttgcaaact gctctaaggg      2400
aatggttcaa gtggaataag tatttgccct ctcgtattat tgtgtatcgt gatggtgtag      2460
gagatggaca gctcaatact ttagtgaact atgaagtgcc tcagtttctg gattgcttga      2520
agactgttgg taaagactac aatccaagac tgactgtgat cgttgtgaag aaacgagtga      2580
gtaccagatt ctttgcgcag gctggtggag gacttaaaaa cccacccccct ggtactgtcg      2640 ttgatataga ggtgaccaga ccagaatggt atgatttctt tattgtgagt caggcagtga      2700
gaaatggttg tgtcgcaccc actcattata acgtagtgta tgacactagc aaactgaaac      2760
cagatcatgt acaacgttta acctacaaac tttgccacat gtactataac tggtcgggtg      2820
ttatcagagt acctgctcct tgccagtatg cccataaact ggctttcctt gtgggtcaga      2880
gcattcacag agaaccaaac ctgttgctct cagacagact ttactatctc taattggttt      2940
aaaaaaaaaa aaaagttcct ttctggggaa ggtggaagtg tggtttgggt tggttggttt      3000
gttttcatga gacacaagca ggggtccatg cagttgtgga acttttattt tcactgtagc      3060
gggaaaaaga ttgaagatag cagatctgtg ttttgaataa gactttattc aactgcatag      3120
agggaaacat tgttagagac tgctacagat tcataggtga atgaactcag ttttgtggtt      3180
gacattgttc gttactttc tcatttaata agcattctct tgatttcctg taaggaacat       3240
cagtatctac gtcagcactg ccttgagagg ggggaaaaaa aaaaaaaag agttgtgcta       3300 tttacagggc tttttggttt ttcagctcca gtaattggaa gggcttaggt gtcagttcgg      3360
att                                                                    3363
```

<210> SEQ ID NO 4
<211> LENGTH: 867
<212> TYPE: PRT
<213> ORGANISM: Gallus gallus domesticus

<400> SEQUENCE: 4

Met Thr Gly Arg Ala Arg Ala Arg Ala Arg Gly Arg Pro Pro Gly Gln
1               5                   10                  15

Glu Ala Ala Ile Pro Pro Val Gly Ala Ala Ser Ala Gln Lys Thr Leu
            20                  25                  30

Pro Ser His Pro Ser Glu Gln Arg Gln Ser Leu Gln Pro Cys His Pro
        35                  40                  45

Pro Pro Leu Thr Glu Glu Pro Gly Gly Arg Gly Arg Gln Arg Gly Pro
    50                  55                  60

Gln Asp Ala Pro Lys Thr Leu Gly Leu Gln Ile Ser Ala Gly Phe Gln
65                  70                  75                  80

Glu Leu Ser Leu Ala Asp Arg Gly Gly Arg Arg Asp Phe His Asp
            85                  90                  95

Leu Gly Val Asn Thr Arg Gln Ala Ile Glu His Val Arg Glu Ser Lys

```
                    100                 105                 110
Thr Gly Ser Ser Gly Ala Met Ile Lys Leu Ile Ala Asn Phe Phe Arg
            115                 120                 125
Leu Thr Ser Arg Pro Gln Trp Ala Leu Tyr Gln Tyr His Val Asp Tyr
        130                 135                 140
Asn Pro Glu Met Glu Ala Arg Arg Leu Arg Ser Gly Leu Leu Phe Gln
145                 150                 155                 160
His Glu Asp Leu Ile Gly Lys Thr His Ala Phe Asp Gly Ser Ile Leu
                165                 170                 175
Phe Leu Pro Lys Arg Leu Pro Asn Lys Val Thr Glu Val Tyr Ser Lys
            180                 185                 190
Thr Arg Asn Gly Glu Asp Val Arg Ile Thr Ile Thr Leu Thr Asn Glu
        195                 200                 205
Leu Pro Pro Thr Ser Pro Thr Cys Leu Gln Phe Tyr Asn Ile Ile Phe
210                 215                 220
Arg Arg Leu Leu Lys Met Met Asn Phe Gln Gln Ile Gly Arg Asn Tyr
225                 230                 235                 240
Tyr Asn Pro Lys Asp Pro Val Ser Ile Pro Asn His Arg Leu Met Val
                245                 250                 255
Trp Pro Gly Phe Thr Ser Ser Ile Leu Gln Tyr Glu Ser Ile Met
            260                 265                 270
Leu Cys Ala Asp Val Ser His Lys Ile Leu Arg Ser Glu Thr Val Leu
        275                 280                 285
Asp Phe Met Tyr Ser Leu Tyr Glu Gln Val Glu Glu Arg Arg Phe Arg
        290                 295                 300
Asp Ala Cys Ala Lys Glu Leu Ile Gly Val Ile Val Leu Thr Lys Tyr
305                 310                 315                 320
Asn Asn Arg Thr Tyr Arg Val Asp Asp Ile Asp Trp Asp Ala Asn Pro
                325                 330                 335
Gln Cys Thr Phe Arg Arg Ala Asp Gly Ser Glu Ile Ser Tyr Ile Asp
            340                 345                 350
Tyr Tyr Lys Arg Gln Tyr Asn Gln Asp Ile Ser Asp Leu Asn Gln Pro
        355                 360                 365
Val Leu Ile Ser Gln Tyr Arg Arg Lys Arg Gly Asn Val Thr Val Gly
    370                 375                 380
Pro Val Val Leu Ile Pro Glu Leu Cys Tyr Leu Thr Gly Leu Thr Glu
385                 390                 395                 400
Lys Met Arg Asn Asp Phe Asn Met Met Lys Asp Leu Ala Val His Thr
                405                 410                 415
Arg Leu Ser Pro Glu Gln Arg Gln Arg Glu Ile Gly Lys Leu Val Asp
            420                 425                 430
Cys Met Lys Lys Asp Glu Cys Val Gln Lys Glu Leu Arg Asp Trp Gly
        435                 440                 445
Leu Ser Phe Asp Ser Ser Leu Leu Ser Phe Thr Gly Arg Val Val Gln
        450                 455                 460
Ala Glu Lys Ile Leu Gln Ala Gly Asn Val Phe Asp Tyr Asn Pro Gln
465                 470                 475                 480
Phe Ala Asp Trp Ser Arg Glu Thr Arg Val Ala Pro Leu Ile His Ala
                485                 490                 495
Lys Pro Leu Asp Asn Trp Leu Leu Ile Tyr Thr Arg Arg Asn Tyr Asp
            500                 505                 510
Ala Ala Asn Met Leu Leu Gln Asn Leu Phe Lys Val Thr Pro Ser Met
        515                 520                 525
```

| | | | | | | | | | | | | |
|---|---|---|---|---|---|---|---|---|---|---|---|---|
|Gly|Ile|Arg|Met|Asn|Lys|Ala|Thr|Met|Ile|Glu|Val|Asp|Asp|Arg|Thr|
|530| | | | |535| | | | |540| | | | | |

Gly Ile Arg Met Asn Lys Ala Thr Met Ile Glu Val Asp Asp Arg Thr
530                535                540

Glu Ala Tyr Leu Arg Val Leu Gln Gln Ser Ile Thr Pro Asp Thr Asn
545                550                555                560

Ile Val Val Cys Ile Leu Ser Ser Thr Arg Lys Asp Lys Tyr Asp Ala
                565                570                575

Ile Lys Lys Tyr Leu Cys Thr Asp Cys Pro Ile Pro Ser Gln Cys Val
                580                585                590

Val Ala Arg Thr Leu Ser Lys Pro Gln Thr Ala Leu Ala Ile Val Thr
                595                600                605

Lys Ile Ala Leu Gln Met Asn Cys Lys Met Gly Gly Glu Leu Trp Ser
610                615                620

Val Glu Ile Pro Leu Lys Gln Leu Met Ile Val Gly Ile Asp Cys Tyr
625                630                635                640

His Asp Thr Leu Ser Gly Lys Gln Ser Ile Ala Gly Phe Val Ala Ser
                645                650                655

Leu Asn Glu Lys Met Thr Arg Trp Phe Ser Arg Cys Val Val Gln Ser
                660                665                670

Arg Gly Gln Glu Ile Val Asp Gly Leu Lys Ala Cys Leu Gln Thr Ala
                675                680                685

Leu Arg Glu Trp Phe Lys Trp Asn Lys Tyr Leu Pro Ser Arg Ile Ile
690                695                700

Val Tyr Arg Asp Gly Val Gly Asp Gly Gln Leu Asn Thr Leu Val Asn
705                710                715                720

Tyr Glu Val Pro Gln Phe Leu Asp Cys Leu Lys Thr Val Gly Lys Asp
                725                730                735

Tyr Asn Pro Arg Leu Thr Val Ile Val Val Lys Lys Arg Val Ser Thr
                740                745                750

Arg Phe Phe Ala Gln Ala Gly Gly Leu Lys Asn Pro Pro Gly
                755                760                765

Thr Val Val Asp Ile Glu Val Thr Arg Pro Glu Trp Tyr Asp Phe Phe
770                775                780

Ile Val Ser Gln Ala Val Arg Asn Gly Cys Val Ala Pro Thr His Tyr
785                790                795                800

Asn Val Val Tyr Asp Thr Ser Lys Leu Lys Pro Asp His Val Gln Arg
                805                810                815

Leu Thr Tyr Lys Leu Cys His Met Tyr Tyr Asn Trp Ser Gly Val Ile
                820                825                830

Arg Val Pro Ala Pro Cys Gln Tyr Ala His Lys Leu Ala Phe Leu Val
                835                840                845

Gly Gln Ser Ile His Arg Glu Pro Asn Leu Leu Leu Ser Asp Arg Leu
850                855                860

Tyr Tyr Leu
865

<210> SEQ ID NO 5
<211> LENGTH: 1989
<212> TYPE: DNA
<213> ORGANISM: Gallus gallus domesticus

<400> SEQUENCE: 5
atggaggagg actgggacac ggagctggag caggaggcgg cagcggcttc ccaggggcgt      60
tctgaggagc aggcgtggat ggctaactct ggcagaccaa acagcccatc cctccgcttc     120
tccagcagac caagcagccc cttgtctggc ttcccaggca gaccaaacag ccccttcttt     180

-continued

| | |
|---|---|
| ggctttagtc agaataaagg ctcacttggt gctaatgaag gacttaacag aagtctgcct | 240 |
| gtgcagcatg acattggagg atattctggg agcagagagt ctgttgtacg tcaaaacaga | 300 |
| gaagatcaac cagtgactag atttggtaga gggaggagtt ctggaagcag agattttcaa | 360 |
| gagaggaact ctgcaaatga tcctggtatg caagatcaag gttttagaag agttcctggc | 420 |
| atctttgggc aaagcaagtg ttttaacagt gaggaaagaa atagtcctct gcgtggcagc | 480 |
| cctttttgccc caggaggaag aggagcagtt ggaggtcctg caggagttct caaaggacgc | 540 |
| tctgaagaaa ttgattctgg aagaggtcca aaggtgactt atgtcccccc tcctccacct | 600 |
| gaagatgaac agtccatctt tgcatgttat cagtcaggaa ttaattttga caagtatgat | 660 |
| gaatgtgctg ttgagatgtc aggacttgac cctccagcac cattactggc ttttgaagaa | 720 |
| gctaactttg ctcagacttt aaggaagaat atatctaaaa ctggatattc aaaacttact | 780 |
| ccagtgcaga agcacagcat tcctgttata caagcagggc gggatttaat gtcatgtgcc | 840 |
| cagacaggat caggaaaaac agcagctttt cttctaccaa ttgtggaccg atgatgaaa | 900 |
| gatggtgtaa ctgcaagctt cccaaagcag caagacccac aatgcattat tgttgcacca | 960 |
| actagagaac tgataaatca gatcttctta gaagcaagga gtttgtgta tgggacttgt | 1020 |
| ataaggcctg ttgtgatcta tggaggtaca cagacaggtc attcaatccg tcaaataatg | 1080 |
| caaggctgta atatattatg tgccactcct ggaaggcttc ttgacattat tgaaaaaggg | 1140 |
| aagatcagtt tggtggaggt gaaatatttg gtactagatg aagcagaccg catgctcgat | 1200 |
| atgggttttg gattagatat gaagaagctg atttcttatc cagaaatgcc atctaaagac | 1260 |
| agacgtcaaa cattaatgtt tagtgccact tttcctgagg aagttcaaag gctggctggt | 1320 |
| gaattttga aaacggacta tatatttctt gttattggaa ataccgtgg agcctgcagt | 1380 |
| gatgttcagc aaaatattct tcaggttccc cggttatcca agaggataa actaatagaa | 1440 |
| attctacaaa gcacaggtgg tgaacgaacc atggtgtttg tggacacaaa gaaaaaagca | 1500 |
| gattaccttg cagccttttct ttgtcaagag aacctaccat ccaccagcat tcatggagat | 1560 |
| agggaacaga gagagagaga gatagctctt cgcgatttcc gttctggaaa atgtcaaatt | 1620 |
| cttgtggcaa cttcggtagc atcaagaggc ctggatattg aaaatgttca acatgttatt | 1680 |
| aattttgatc tccctaacac cattgaagat tatgtacatc gaattggacg aactggtcgt | 1740 |
| tgtgaaata ctggcaaagc agtttcattc tttgatgatc agtcagatgg ccatcttgta | 1800 |
| caatcactac ttaaagtgct tccagaacc cagcaggaat ccagtttgg tggaagaatg | 1860 |
| gctgtccaaa gaacaaatat tgttgcttca acttggtgcc caagggatt aatgcaggcc | 1920 |
| gtggcagaat ggaacccaag agaaatgagg atgtcatatt ctgaaacaac atttaagtca | 1980 |
| tgggagtaa | 1989 |

<210> SEQ ID NO 6
<211> LENGTH: 662
<212> TYPE: PRT
<213> ORGANISM: Gallus gallus domesticus

<400> SEQUENCE: 6

Met Glu Glu Asp Trp Asp Thr Glu Leu Glu Gln Glu Ala Ala Ala Ala
1               5                   10                  15

Ser Gln Gly Arg Ser Glu Glu Gln Ala Trp Met Ala Asn Ser Gly Arg
            20                  25                  30

Pro Asn Ser Pro Ser Leu Arg Phe Ser Arg Pro Ser Ser Pro Leu
        35                  40                  45

Ser Gly Phe Pro Gly Arg Pro Asn Ser Pro Phe Phe Gly Phe Ser Gln

```
                50                  55                  60
Asn Lys Gly Ser Leu Gly Ala Asn Glu Gly Leu Asn Arg Ser Leu Pro
 65                  70                  75                  80

Val Gln His Asp Ile Gly Gly Tyr Ser Gly Ser Arg Glu Ser Val Val
                     85                  90                  95

Arg Gln Asn Arg Glu Asp Gln Pro Val Thr Arg Phe Gly Arg Gly Arg
                100                 105                 110

Ser Ser Gly Ser Arg Asp Phe Gln Glu Arg Asn Ser Ala Asn Asp Pro
                115                 120                 125

Gly Met Gln Asp Gln Gly Phe Arg Arg Val Pro Gly Ile Phe Gly Gln
                130                 135                 140

Ser Lys Cys Phe Asn Ser Glu Glu Arg Asn Ser Pro Leu Arg Gly Ser
145                 150                 155                 160

Pro Phe Ala Pro Gly Gly Arg Gly Ala Val Gly Gly Pro Ala Gly Val
                165                 170                 175

Leu Lys Gly Arg Ser Glu Glu Ile Asp Ser Gly Arg Gly Pro Lys Val
                180                 185                 190

Thr Tyr Val Pro Pro Pro Pro Glu Asp Glu Gln Ser Ile Phe Ala
                195                 200                 205

Cys Tyr Gln Ser Gly Ile Asn Phe Asp Lys Tyr Asp Glu Cys Ala Val
                210                 215                 220

Glu Met Ser Gly Leu Asp Pro Pro Ala Pro Leu Ala Phe Glu Glu
225                 230                 235                 240

Ala Asn Phe Ala Gln Thr Leu Arg Lys Asn Ile Ser Lys Thr Gly Tyr
                245                 250                 255

Ser Lys Leu Thr Pro Val Gln Lys His Ser Ile Pro Val Ile Gln Ala
                260                 265                 270

Gly Arg Asp Leu Met Ser Cys Ala Gln Thr Gly Ser Gly Lys Thr Ala
                275                 280                 285

Ala Phe Leu Leu Pro Ile Val Asp Arg Met Met Lys Asp Gly Val Thr
                290                 295                 300

Ala Ser Phe Pro Lys Gln Gln Asp Pro Gln Cys Ile Ile Val Ala Pro
305                 310                 315                 320

Thr Arg Glu Leu Ile Asn Gln Ile Phe Leu Glu Ala Arg Lys Phe Val
                325                 330                 335

Tyr Gly Thr Cys Ile Arg Pro Val Val Ile Tyr Gly Gly Thr Gln Thr
                340                 345                 350

Gly His Ser Ile Arg Gln Ile Met Gln Gly Cys Asn Ile Leu Cys Ala
                355                 360                 365

Thr Pro Gly Arg Leu Leu Asp Ile Ile Glu Lys Gly Lys Ile Ser Leu
                370                 375                 380

Val Glu Val Lys Tyr Leu Val Leu Asp Glu Ala Asp Arg Met Leu Asp
385                 390                 395                 400

Met Gly Phe Gly Leu Asp Met Lys Lys Leu Ile Ser Tyr Pro Glu Met
                405                 410                 415

Pro Ser Lys Asp Arg Arg Gln Thr Leu Met Phe Ser Ala Thr Phe Pro
                420                 425                 430

Glu Glu Val Gln Arg Leu Ala Gly Glu Phe Leu Lys Thr Asp Tyr Ile
                435                 440                 445

Phe Leu Val Ile Gly Asn Thr Cys Gly Ala Cys Ser Asp Val Gln Gln
                450                 455                 460

Asn Ile Leu Gln Val Pro Arg Leu Ser Lys Arg Asp Lys Leu Ile Glu
465                 470                 475                 480
```

```
Ile Leu Gln Ser Thr Gly Gly Glu Arg Thr Met Val Phe Val Asp Thr
            485                 490                 495

Lys Lys Lys Ala Asp Tyr Leu Ala Ala Phe Leu Cys Gln Glu Asn Leu
        500                 505                 510

Pro Ser Thr Ser Ile His Gly Asp Arg Glu Gln Arg Glu Arg Glu Ile
    515                 520                 525

Ala Leu Arg Asp Phe Arg Ser Gly Lys Cys Gln Ile Leu Val Ala Thr
530                 535                 540

Ser Val Ala Ser Arg Gly Leu Asp Ile Glu Asn Val Gln His Val Ile
545                 550                 555                 560

Asn Phe Asp Leu Pro Asn Thr Ile Glu Asp Tyr Val His Arg Ile Gly
                565                 570                 575

Arg Thr Gly Arg Cys Gly Asn Thr Gly Lys Ala Val Ser Phe Phe Asp
            580                 585                 590

Asp Gln Ser Asp Gly His Leu Val Gln Ser Leu Leu Lys Val Leu Ser
            595                 600                 605

Arg Thr Gln Gln Glu Phe Gln Phe Gly Gly Arg Met Ala Val Gln Arg
        610                 615                 620

Thr Asn Ile Val Ala Ser Thr Trp Cys Pro Lys Gly Leu Met Gln Ala
625                 630                 635                 640

Val Ala Glu Trp Asn Pro Arg Glu Met Arg Met Ser Tyr Ser Glu Thr
                645                 650                 655

Thr Phe Lys Ser Trp Glu
            660
```

```
<210> SEQ ID NO 7
<211> LENGTH: 561
<212> TYPE: DNA
<213> ORGANISM: Gallus gallus domesticus

<400> SEQUENCE: 7
cgggcgctgc tggggacgag ctctgcgtgt cccaccaacg ggctgtgccg ggccaatgtc      60
ctggagcaga cccgcaggca ggtcgcactg ctcaacgcca ccgcgcagga cctcttcagc     120
ctctatctga agtgccaggg agagccgttc agcagcgaga gcgaccgcct ctgcagcccc     180
agtggcatct tcttcccccc cttccacgtc aaccggacca ccgagaggaa ggaggtgatg     240
gtggccatgt acaagctctt cgccttcctc aacgcctcac tggggaacat cacccgcgac     300
caggaggagc tcaaccccat ggccaaggag ctcctcaacc gcctccacaa caccaccaaa     360
accacgcggg gcctcatctc caacctcacc tgcctgctct gcaagcacta acacatcttc     420
caggtggacg tgagctacgg ggagagcagc aaggacaaga gcgccttcaa gaagaagcag     480
cagggctgcc aggtgctcag gaagtacgtg caggtcatcg cccaggctgc tcgtgtcctc     540
ctacctcacc tcagccccgc g                                               561
```

```
<210> SEQ ID NO 8
<211> LENGTH: 187
<212> TYPE: PRT
<213> ORGANISM: Gallus gallus domesticus

<400> SEQUENCE: 8

Arg Ala Leu Leu Gly Thr Ser Ser Ala Cys Pro Thr Asn Gly Leu Cys
1               5                   10                  15

Arg Ala Asn Val Leu Glu Gln Thr Arg Arg Gln Val Ala Leu Leu Asn
            20                  25                  30

Ala Thr Ala Gln Asp Leu Phe Ser Leu Tyr Leu Lys Cys Gln Gly Glu
        35                  40                  45
```

```
Pro Phe Ser Ser Glu Ser Asp Arg Leu Cys Ser Pro Ser Gly Ile Phe
            50                  55                  60

Phe Pro Pro Phe His Val Asn Arg Thr Thr Glu Arg Lys Glu Val Met
 65                  70                  75                  80

Val Ala Met Tyr Lys Leu Phe Ala Phe Leu Asn Ala Ser Leu Gly Asn
                 85                  90                  95

Ile Thr Arg Asp Gln Glu Glu Leu Asn Pro Met Ala Lys Glu Leu Leu
                100                 105                 110

Asn Arg Leu His Asn Thr Thr Lys Thr Thr Arg Gly Leu Ile Ser Asn
            115                 120                 125

Leu Thr Cys Leu Leu Cys Lys His Tyr Asn Ile Phe Gln Val Asp Val
130                 135                 140

Ser Tyr Gly Glu Ser Ser Lys Asp Lys Ser Ala Phe Lys Lys Lys Gln
145                 150                 155                 160

Gln Gly Cys Gln Val Leu Arg Lys Tyr Val Gln Val Ile Ala Gln Ala
                165                 170                 175

Ala Arg Val Leu Leu Pro His Leu Ser Pro Ala
            180                 185

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 9
atgacagctt gcaggcagaa g                                              21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 10
cgtacaggag agctcgagaa ctg                                            23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 11
ccaggattca caagttctat tc                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 12
gcacaggcat ctctaaatct tc                                             22
```

```
<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 13
cgtggcagcc cttttgc                                                    17

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 14
ttcagagcgt cctttgagaa ctc                                             23

<210> SEQ ID NO 15
<211> LENGTH: 259
<212> TYPE: PRT
<213> ORGANISM: Gallus gallus domesticus

<400> SEQUENCE: 15
```

Pro Val Ser Ile Pro Asn His Arg Leu Met Val Trp Pro Gly Phe Thr
 1               5                  10                  15

Ser Ser Ile Leu Gln Tyr Glu Glu Ser Ile Met Leu Cys Ala Asp Val
            20                  25                  30

Ser His Lys Ile Leu Arg Ser Glu Thr Val Leu Asp Phe Met Tyr Ser
        35                  40                  45

Leu Tyr Glu Gln Val Glu Glu Arg Arg Phe Arg Asp Ala Cys Ala Lys
    50                  55                  60

Glu Leu Ile Gly Val Ile Val Leu Thr Lys Tyr Asn Asn Arg Thr Tyr
65                  70                  75                  80

Arg Val Asp Asp Ile Asp Trp Asp Ala Asn Pro Gln Cys Thr Phe Arg
                85                  90                  95

Arg Ala Asp Gly Ser Glu Ile Ser Tyr Ile Asp Tyr Tyr Lys Arg Gln
            100                 105                 110

Tyr Asn Gln Asp Ile Ser Asp Leu Asn Gln Pro Val Leu Ile Ser Gln
        115                 120                 125

Tyr Arg Arg Lys Arg Gly Asn Val Thr Val Gly Pro Val Val Leu Ile
    130                 135                 140

Pro Glu Leu Cys Tyr Leu Thr Gly Leu Thr Glu Lys Met Arg Asn Asp
145                 150                 155                 160

Phe Asn Met Met Lys Asp Leu Ala Val His Thr Arg Leu Ser Pro Glu
                165                 170                 175

Gln Arg Gln Arg Glu Ile Gly Lys Leu Val Asp Cys Met Lys Lys Asp
            180                 185                 190

Glu Cys Val Gln Lys Glu Leu Arg Asp Trp Gly Leu Ser Phe Asp Ser
        195                 200                 205

Ser Leu Leu Ser Phe Thr Gly Arg Val Val Gln Ala Glu Lys Ile Leu
    210                 215                 220

Gln Ala Gly Asn Val Phe Asp Tyr Asn Pro Gln Phe Ala Asp Trp Ser
225                 230                 235                 240

Arg Glu Thr Arg Val Ala Pro Leu Ile His Ala Lys Pro Leu Asp Asn

Trp Leu Leu

<210> SEQ ID NO 16
<211> LENGTH: 349
<212> TYPE: PRT
<213> ORGANISM: Gallus gallus domesticus

<400> SEQUENCE: 16

Ser Arg Asp Phe Gln Glu Arg Asn Ser Ala Asn Asp Pro Gly Met Gln
1               5                   10                  15

Asp Gln Gly Phe Arg Arg Val Pro Gly Ile Phe Gly Gln Ser Lys Cys
            20                  25                  30

Phe Asn Ser Glu Glu Arg Asn Ser Pro Leu Arg Gly Ser Pro Phe Ala
        35                  40                  45

Pro Gly Gly Arg Gly Ala Val Gly Gly Pro Ala Gly Val Leu Lys Gly
    50                  55                  60

Arg Ser Glu Glu Ile Asp Ser Gly Arg Gly Pro Lys Val Thr Tyr Val
65                  70                  75                  80

Pro Pro Pro Pro Glu Asp Glu Gln Ser Ile Phe Ala Cys Tyr Gln
                85                  90                  95

Ser Gly Ile Asn Phe Asp Lys Tyr Asp Glu Cys Ala Val Glu Met Ser
                100                 105                 110

Gly Leu Asp Pro Pro Ala Pro Leu Leu Ala Phe Glu Glu Ala Asn Phe
            115                 120                 125

Ala Gln Thr Leu Arg Lys Asn Ile Ser Lys Thr Gly Tyr Ser Lys Leu
        130                 135                 140

Thr Pro Val Gln Lys His Ser Ile Pro Val Ile Gln Ala Gly Arg Asp
145                 150                 155                 160

Leu Met Ser Cys Ala Gln Thr Gly Ser Gly Lys Thr Ala Ala Phe Leu
                165                 170                 175

Leu Pro Ile Val Asp Arg Met Met Lys Asp Gly Val Thr Ala Ser Phe
            180                 185                 190

Pro Lys Gln Gln Asp Pro Gln Cys Ile Ile Val Ala Pro Thr Arg Glu
        195                 200                 205

Leu Ile Asn Gln Ile Phe Leu Glu Ala Arg Lys Phe Val Tyr Gly Thr
    210                 215                 220

Cys Ile Arg Pro Val Val Ile Tyr Gly Gly Thr Gln Thr Gly His Ser
225                 230                 235                 240

Ile Arg Gln Ile Met Gln Gly Cys Asn Ile Leu Cys Ala Thr Pro Gly
                245                 250                 255

Arg Leu Leu Asp Ile Ile Glu Lys Gly Lys Ile Ser Leu Val Glu Val
            260                 265                 270

Lys Tyr Leu Val Leu Asp Glu Ala Asp Arg Met Leu Asp Met Gly Phe
        275                 280                 285

Gly Leu Asp Met Lys Lys Leu Ile Ser Tyr Pro Glu Met Pro Ser Lys
    290                 295                 300

Asp Arg Arg Gln Thr Leu Met Phe Ser Ala Thr Phe Pro Glu Glu Val
305                 310                 315                 320

Gln Arg Leu Ala Gly Glu Phe Leu Lys Thr Asp Tyr Ile Phe Leu Val
                325                 330                 335

Ile Gly Asn Thr Cys Gly Ala Cys Ser Asp Val Gln Gln
            340                 345

<210> SEQ ID NO 17

-continued

```
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 17
gtaaacggcc acaagttcag                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide for PCR Primer

<400> SEQUENCE: 18
cttgtacagc tcgtccatgc                                                 20

<210> SEQ ID NO 19
<211> LENGTH: 305
<212> TYPE: PRT
<213> ORGANISM: Homo sapiens

<400> SEQUENCE: 19

Met Ser Val Asp Pro Ala Cys Pro Gln Ser Leu Pro Cys Phe Glu Ala
 1               5                  10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255
```

```
Asn Ser Pro Ala Ser Asp Leu Glu Ala Ala Leu Glu Ala Ala Gly Glu
              260                 265                 270

Gly Leu Asn Val Ile Gln Gln Thr Thr Arg Tyr Phe Ser Thr Pro Gln
              275                 280                 285

Thr Met Asp Leu Phe Leu Asn Tyr Ser Met Asn Met Gln Pro Glu Asp
              290                 295                 300

Val
305

<210> SEQ ID NO 20
<211> LENGTH: 305
<212> TYPE: PRT
<213> ORGANISM: Mus musculus

<400> SEQUENCE: 20

Met Ser Val Gly Leu Pro Gly Pro His Ser Leu Pro Ser Ser Glu Glu
  1               5                  10                  15

Ala Ser Asn Ser Gly Asn Ala Ser Ser Met Pro Ala Val Phe His Pro
               20                  25                  30

Glu Asn Tyr Ser Cys Leu Gln Gly Ser Ala Thr Glu Met Leu Cys Thr
           35                  40                  45

Glu Ala Ala Ser Pro Arg Pro Ser Ser Glu Asp Leu Pro Leu Gln Gly
 50                  55                  60

Ser Pro Asp Ser Ser Thr Ser Pro Lys Gln Lys Leu Ser Ser Pro Glu
 65                  70                  75                  80

Ala Asp Lys Gly Pro Glu Glu Glu Asn Lys Val Leu Ala Arg Lys
                 85                  90                  95

Gln Lys Met Arg Thr Val Phe Ser Gln Ala Gln Leu Cys Ala Leu Lys
                100                 105                 110

Asp Arg Phe Gln Lys Gln Lys Tyr Leu Ser Leu Gln Gln Met Gln Glu
            115                 120                 125

Leu Ser Ser Ile Leu Asn Leu Ser Tyr Lys Gln Val Lys Thr Trp Phe
130                 135                 140

Gln Asn Gln Arg Val Lys Cys Lys Arg Trp Gln Lys Asn Gln Trp Leu
145                 150                 155                 160

Lys Thr Ser Asn Gly Leu Ile Gln Lys Gly Ser Ala Pro Val Glu Tyr
                165                 170                 175

Pro Ser Ile His Cys Ser Tyr Pro Gln Gly Tyr Leu Val Asn Ala Ser
            180                 185                 190

Gly Ser Leu Ser Met Trp Gly Ser Gln Thr Trp Thr Asn Pro Thr Trp
            195                 200                 205

Ser Ser Gln Thr Trp Thr Asn Pro Thr Trp Asn Asn Gln Thr Trp Thr
210                 215                 220

Asn Pro Thr Trp Ser Ser Gln Ala Trp Thr Ala Gln Ser Trp Asn Gly
225                 230                 235                 240

Gln Pro Trp Asn Ala Ala Pro Leu His Asn Phe Gly Glu Asp Phe Leu
                245                 250                 255

Gln Pro Tyr Val Gln Leu Gln Gln Asn Phe Ser Ala Ser Asp Leu Glu
            260                 265                 270

Val Asn Leu Glu Ala Thr Arg Glu Ser His Ala His Phe Ser Thr Pro
275                 280                 285

Gln Ala Leu Glu Leu Phe Leu Asn Tyr Ser Val Thr Pro Pro Gly Glu
            290                 295                 300

Ile
305
```

METHOD OF DETERMINING CHICKEN EMBRYONIC STEM CELLS

TECHNICAL FIELD

The present invention relates to chicken embryonic stem cells and a method for evaluation thereof. More specifically, the present invention relates to chicken embryonic stem cells applicable to genetic modification technique and a method for evaluation to appropriately determine whether or not the chicken embryonic stem cells are applicable to the genetic modification technique.

BACKGROUND ART

Embryonic stem cells (ES cells) are undifferentiated cells each of which is isolated from an early stage embryo and has pluripotency, and it is known that the ES cells not only have the pluripotency (an ability of being differentiated into three germ layers) but also have an ability of self-replication. Such the ES cells are now being vigorously studied in various fields such as the regenerative medicine. Moreover, mouse ES cells are widely utilized for e.g., production of a mouse in which a specific gene is modified by means of gene targeting.

In recent years, functional analysis of genes inherent to living things has been dramatically improved by production of animals to which a specific gene is introduced or animals in which a specific gene is knocked out. These animals i.e., the genetically modified animals have been utilized in wide research fields in addition to the medical biology, and have greatly contributed to progress in research and development in each field.

In order to apply ES cells to genetic modification technique, it is further required that the ES cells can be differentiated into germ cells. However, except for ES cells of a mouse, there has not been reported so far any ES cells of animal species which ES cells have the pluripotency and the ability of being differentiated into germ cells. Therefore, with respect to animal species except for a mouse, it is necessary to develop a method for establishment of ES cells and a method for evaluation of the ES cells.

It has been reported that chicken ES cells were established (see Non-Patent Literatures 1 to 3). According to these reports, leukemia inhibitory factor (LIF) derived from a mouse and family factors thereof were used as a factor to be added to a medium in order to cause the chicken ES cells to maintain its pluripotency. Further, Non-Patent Literatures 2 and 3 report that ES cells were established by using a culture supernatant of buffalo rat liver (BRL) cells.

Citation List
Patent Literature 1
Japanese Patent Application Publication, Tokukai, No. 2003-9869 A (Publication Date: Jan. 14, 2003)
Patent Literature 2
WO 2006/054666 A1 Pamphlet (International Publication Date May 26, 2006)
Non-Patent Literature 1
Pain B. et al. Development 122(8): 2339-2348 (1996)
Non-Patent Literature 2
van de Lavoir M C. et al. Mech. Dev. 123(1): 31-41 (2006)
Non-Patent Literature 3
van de Lavoir M C. and Mather-Love C. Methods Enzymol. 418: 38-64 (2006)
Non-Patent Literature 4
Horiuchi H. et al. J. Biol. Chem. 279(23): 24514-24520 (2004)
Non-Patent Literature 5
Yamashita Y. et al. Dev. Comp. Immunol. 30(5): 513-22 (2006)
Non-Patent Literature 6
Mitsui K. et al. Cell 113(5): 631-642 (2003)
Non-Patent Literature 7
Chambers I. et al. Cell 113(5): 643-655 (2003)
Non-Patent Literature 8
van de Lavoir M C. et al. Nature 441: 766-769 (2006)

SUMMARY OF INVENTION

However, chicken ES cells described in Non-Patent Literature 1 lost its pluripotency after long-term serial passage (10 days or longer) (see Non-Patent Literatures 4 and 5 and Patent Literature 1). Further, specific effects that the BRL culture supernatant described in Non-Patent Literatures 2 and 3 gives are unclear. Furthermore, in the ES cells produced in this method, expression of CVH (chicken Vasa homologue; a molecule which is specifically expressed in germ line cells and is an indicator indicative of whether or not the cells have the ability of being differentiated into germ cells) is not observed, and therefore the ES cells lacks the ability of being differentiated into germ cells (see Non-Patent Literature 8). Thus, the chicken ES cells reported so far do not have the feature of "having pluripotency and an ability of being differentiated into germ cells". Therefore, it is impossible to apply these chicken ES cells to genetic modification technique.

The present invention was made in view of the foregoing problems, and an object of the present invention is to establish a chicken ES cell applicable to genetic modification technique and to provide a method for evaluation to determine whether or not the chicken ES cell is applicable to the genetic modification technique.

A chicken embryonic stem cell according to the present invention stably has the pluripotency and the ability of being differentiated into a germ cell. With this feature, the present invention is applicable to production of a genetically modified chicken.

It is preferable that, in the chicken embryonic stem cell according to the present invention, both of Sachi-1 protein and CVH protein are stably expressed. Sachi-1 protein refers to (a) a protein having the amino acid sequence shown in SEQ ID NO: 2, and CVH protein refers to (b) a protein having the amino acid sequence shown in SEQ ID NO: 6.

It is more preferable that, in the chicken embryonic stem cell according to the present invention, chiwi protein is stably expressed in addition to Sachi-1 protein and CVH protein. Chiwi protein refers to (c) a protein having the amino acid sequence shown in SEQ ID NO: 4.

It is preferable that, in the chicken embryonic stem cell according to the present invention, both of an mRNA of Sachi-1 and an mRNA of CVH are stably expressed. The mRNA of Sachi-1 refers to a polynucleotide having a sequence complementary to the base sequence shown in SEQ ID NO: 1, and the mRNA of CVH refers to a polynucleotide having a sequence complementary to the base sequence shown in SEQ ID NO: 5.

Further, it is more preferable that, in the chicken embryonic stem cell according to the present invention, an mRNA of chiwi is stably expressed in addition to the mRNAs of Sachi-1 and CVH. The mRNA of chiwi refers to a polynucleotide having a sequence complementary to the base sequence shown in SEQ ID NO: 3.

A method for evaluation of a chicken embryonic stem cell according to the present invention comprises the step of detecting whether or not the chicken embryonic stem cell stably has the pluripotency and the ability of being differentiated into a germ cell. With this feature, the present invention can carry out evaluation to determine whether or not the embryonic stem cell is available for production of a genetically modified chicken.

It is preferable that, in the method for evaluation according to the present invention, said step of detecting is carried out at least for 10 days. With this, it is possible to confirm that the embryonic stem cell stably has the pluripotency and the ability of being differentiated into a germ cell.

Further, it is preferable that, in the method for evaluation according to the present invention, said step of detecting is carried out by detection of stable expression of both of Sachi-1 protein and CVH protein in the chicken embryonic stem cell, more specifically, by detection of stable expression of both of (a) a protein having the amino acid sequence shown in SEQ ID NO: 2 and (b) a protein having the amino acid sequence shown in SEQ ID NO: 6 in the chicken embryonic stem cell.

Note that, in the method for evaluation according to the present invention, said step of detecting may be carried out by detection of stable expression of an mRNA of Sachi-1 and an mRNA of CVH in the chicken embryonic stem cell, more specifically, by detection of stable expression of (a') a polynucleotide having a sequence complementary to the base sequence shown in SEQ ID NO: 1 and (b') a polynucleotide having a sequence complementary to the base sequence shown in SEQ ID NO: 5 in the chicken embryonic stem cell.

It is preferable that, in the method for evaluation according to the present invention, said step of detecting is carried out by further detection of stable expression of chiwi protein in the chicken embryonic stem cell, more specifically, by detection of stable expression of (c) a protein having the amino acid sequence shown in SEQ ID NO: 4 in the chicken embryonic stem cell.

Note that, in the method for evaluation according to the present invention, said step of detecting may be carried out by detection of stable expression of an mRNA of chiwi in the chicken embryonic stem cell, more specifically, by detection of stable expression of (c') a polynucleotide having a sequence complementary to the base sequence shown in SEQ ID NO: 3 in the chicken embryonic stem cell.

A kit according to the present invention includes a chicken embryonic stem cell. As described above, a chicken embryonic stem cell according to the present invention is a cell available for production of a genetically modified chicken. The kit according to the present invention may further include a chicken LIF protein.

A method for production of a genetically modified chicken according to the present invention comprises the step of culturing the chicken embryonic stem cell together with a chicken LIF protein. This feature makes it possible to carry out genetic engineering (gene targeting) without causing the chicken embryonic stem cell to be differentiated.

For a fuller understanding of the nature and advantages of the invention, reference should be made to the ensuing detailed description taken in conjunction with the accompanying drawings.

BRIEF DESCRIPTION OF DRAWINGS

FIG. 1

FIG. 1 is a view illustrating the morphology of the colonies of blastodermal cells observed after 3 days in culture.

FIG. 2

FIG. 2 is a view illustrating chicken ES cells stably grown even after being passaged, and (b) is a high magnification view of (a).

FIG. 3

FIG. 3 shows established chicken ES cells (2 lines) which were prepared by thawing its frozen stock ((a) of FIG. 3 shows the cells observed over one year after its establishment; (b) of FIG. 3 shows the cells observed over half a year after its establishment).

FIG. 4

FIG. 4 is a view illustrating (a) an alignment of an amino acid sequence of Sachi-1 with amino acid sequences of mammal Nanog and (b) an identity between the amino acid sequence of Sachi-1 and the amino acid sequences of mammal Nanog determined in a homeodomain.

FIG. 5 is a view showing a result of quantitative expression analysis of a Sachi-1 mRNA carried out by real-time PCR.

FIG. 6

FIG. 6 is a view showing a result of expression analysis on various tissues and cells of chickens carried out by real-time PCR.

FIG. 7

FIG. 7 is a view showing a result of fluorescence antibody technique carried out on blastodermal cells (the area pellucida of the blastoderm). (a) of FIG. 7 shows a transmission image of the cells; (b) of FIG. 7 shows an image of the cells immunostained with anti-Sachi-1 antibody; (c) of FIG. 7 shows an image of the cells immunostained with anti-CVH antibody.

FIG. 8

FIG. 8 is a view showing a result of fluorescence antibody technique carried out on blastodermal cells (the area pellucida of the blastoderm). (a) of FIG. 8 shows a transmission image of the cells; (b) of FIG. 8 shows an image of the cells stained with DAPI; (c) of FIG. 8 shows an image of the cells immunostained with anti-chiwi antibody.

FIG. 9 is a view showing results of fluorescence antibody technique carried out on primordial germ cells (PGCs). Each of (a) and (e) of FIG. 9 shows a transmission image of the cells; each of (b) and (f) of FIG. 9 shows an image of the cells stained with DAPI; (c) of FIG. 9 shows an image of the cells immunostained with anti-Sachi-1 antibody; (d) of FIG. 9 shows an image of the cells immunostained with anti-chiwi antibody; and (g) of FIG. 9 shows an image of the cells immunostained with anti-CVH antibody. The results of (a) to (d) of FIG. 9 were obtained by observation of the same view field, and the results of (e) to (g) of FIG. 9 were obtained by observation of the same view field.

FIG. 10

FIG. 10 is a view showing a result of fluorescence antibody technique carried out on a testis section. (a) of FIG. 10 shows views obtained by observation of CVH-positive cells; (b) of FIG. 10 shows views obtained by observation of chiwi-positive cells (in each of (a) and (b) of FIG. 10, the upper view was observed with a low magnification, and the lower view was observed with a high magnification).

FIG. 11 shows results of fluorescence antibody technique carried out on chicken ES cells of two different lines out of the established chicken ES cells. (a) of FIG. 11 shows transmission images of the cells; (b) of FIG. 11 shows images of the cells immunostained with anti-Sachi-1 antibody; (c) of FIG. 11 shows images of the cells immuno stained with anti-chiwi antibody.

FIG. 12

FIG. 12 is a view illustrating gene expression of the established chicken ES cells, in comparison with that of blastodermal cells having the pluripotency and the ability of being differentiated into germ cells.

FIG. 13

FIG. 13 shows that the established chicken ES cell line maintains its pluripotency and its ability of being differentiated into germ cells even after being subjected to gene introduction. (a) of FIG. 13 shows an image of a bright field; (b) of FIG. 13 shows an image of EGFP fluorescence; (c) of FIG. 13 shows an image of CVH stained with an antibody.

FIG. 14

FIG. 14 shows a result of observation of embryonic blood collected from a recipient embryo 2 to 3 days after interplanted a chicken ES cell line in the recipient embryo. The chicken ES cell line, in which EGFP had been introduced, was CVH positive. (a) of FIG. 14 shows an image of a bright field, and (b) of FIG. 14 shows an image of EGFP fluorescence.

FIG. 15

FIG. 15 shows a result of detection of EGFP existing in the genomic DNAs prepared from the gonads of the chimeras obtained by incubation of the recipient embryos interplanted with the chicken ES cell line into which EGFP had been introduced and which was CVH positive.

FIG. 16

FIG. 16 shows views demonstrating that the established and evaluated chicken ES cells contributed to the germ line. (a) of FIG. 16 shows a chick (upper) and a sexually matured individual (lower) each of which is of a first generation chimeric chicken (G0) produced by interplanting of the ES cells. (b) of FIG. 16 shows a chick (black feather) of G1 generation produced by artificially inseminating the chicken illustrated in (a) of FIG. 16.

DESCRIPTION OF EMBODIMENTS

[1. Chicken Embryonic Stem Cells]

Figure 5:
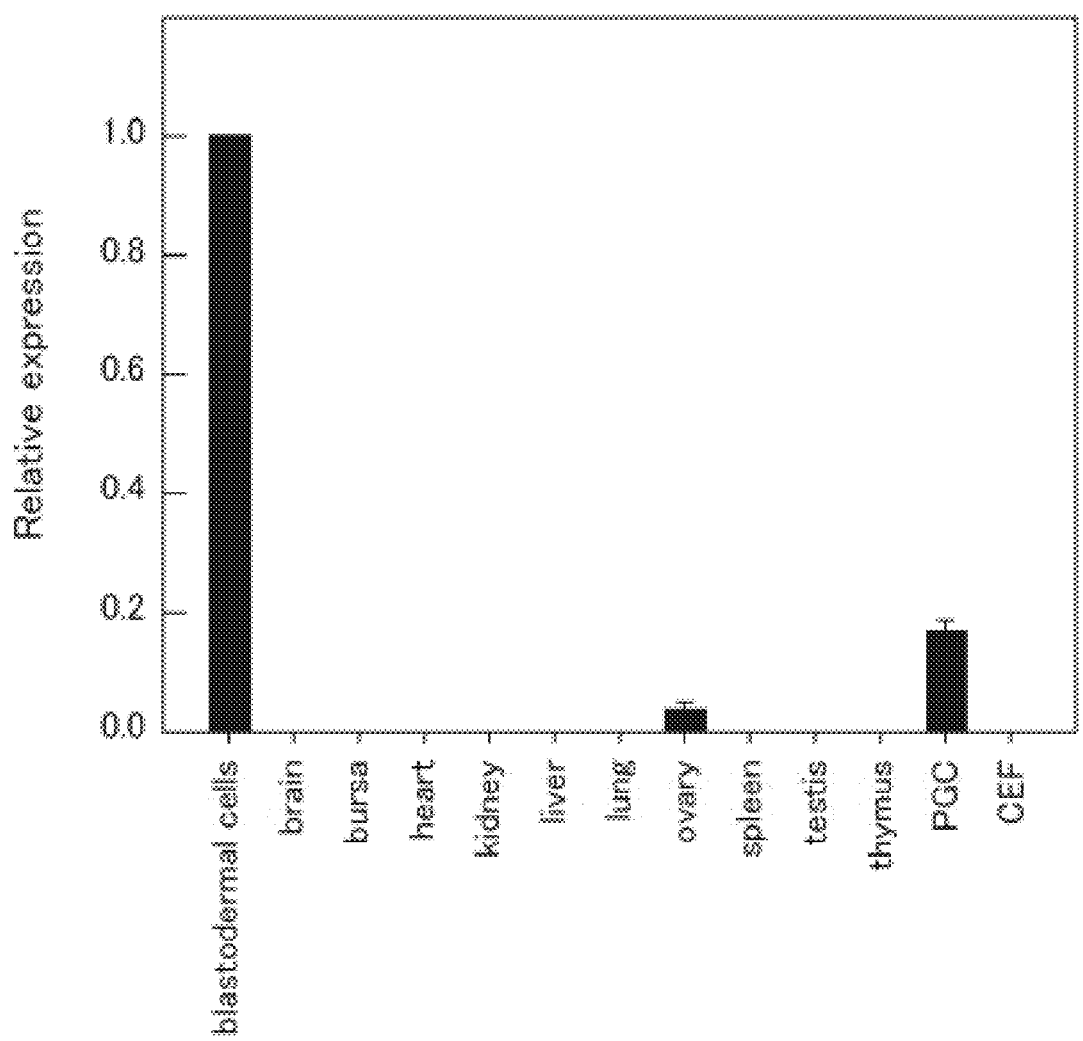
FIG. 5

Chicken embryonic stem (ES) cells according to the present invention stably have pluripotency and an ability of being differentiated into germ cells. So far, there have not been chicken ES cells stably having the pluripotency and the ability of being differentiated into germ cells. With this feature, the chicken ES cells according to the present invention are applicable to production of a genetically modified chicken.

In one aspect, it is preferable that, in a chicken ES cell according to the present invention, both of Sachi-1 protein and CVH protein are stably expressed, and it is more preferable that, in the chicken ES cell according to the present invention, chiwi protein is stably expressed in addition to Sachi-1 protein and CVH protein.

Sachi-1 protein refers to (a) a protein having the amino acid sequence shown in SEQ ID NO: 2, and CVH protein refers to (b) a protein having the amino acid sequence shown in SEQ ID NO: 6. Chiwi protein refers to (c) a protein having the amino acid sequence shown in SEQ ID NO: 4.

As used herein, the term "protein" is used interchangeably with "peptide" or "polypeptide". The "fragment" of a protein refers to a partial fragment of the protein. As used herein, a protein may be isolated from natural sources, or chemically synthesized.

The term "isolated" protein refers to a protein obtained from a natural environment in which the protein resides. For example, a recombinant protein expressed in a host cell can be regarded as being isolated, like a natural or recombinant protein that has been substantially purified by any appropriate techniques.

In another aspect, it is preferable that, in a chicken ES cell according to the present invention, both of an mRNA of Sachi-1 and an mRNA of CVH are stably expressed, and it is more preferable that, in the chicken ES cell according to the present invention, an mRNA of chiwi is stably expressed in addition to the mRNAs of Sachi-1 and CVH.

The mRNA of Sachi-1 refers to a polynucleotide having a sequence complementary to the base sequence shown in SEQ ID NO: 1, and the mRNA of CVH refers to a polynucleotide having a sequence complementary to the base sequence shown in SEQ ID NO: 5. The mRNA of chiwi refers to a polynucleotide having a sequence complementary to the base sequence shown in SEQ ID NO: 3.

As used herein, the term "polypeptide" is used interchangeably with "gene", "nucleic acid", or "nucleic acid molecule", and refers to a polymer of nucleotides. As used herein, the term "base sequence" is used interchangeably with "nucleic acid sequence" or "nucleotide sequence", and it is represented by a sequence of deoxyribonucleotides (abbreviated as A, G, C, and T). The "fragment" of a polynucleotide refers to a partial fragment of the polynucleotide. As used herein, a polynucleotide may be isolated from natural sources, recombinantly produced, or chemically synthesized.

As used herein, a polynucleotide may be in the form of RNA (e.g., mRNA) or DNA (e.g., cDNA or genomic DNA). The DNA may be double stranded or single stranded. The single stranded DNA or RNA may be a coding strand (also known as a sense strand) or a non-coding strand (also known as anti-sense strand).

The term "isolated" polynucleotide refers to a polynucleotide obtained from a natural environment in which the polynucleotide resides. For example, a polynucleotide expressed in a host cell can be considered as being isolated, like a natural or recombinant polynucleotide that has been substantially purified by any appropriate techniques.

It is preferable that EmbryoMax DMEM (manufactured by Chemicon) is used as a medium for use in establishment of chicken ES cells according to the present invention (chicken ES cell stably having the pluripotency and the ability of being differentiated into germ cells). However, the present invention is not limited to this.

It is preferable that an STO cell or a chicken embryo fibroblast (CEF) cell is used as a supporting cell (feeder cell) for use in establishment of chicken ES cells according to the present invention. However, the present invention is not limited to this. A person skilled in the art can readily prepare CEF cells from the chicken tissues. However, in order to prevent malignant alteration of the cells due to e.g., a virus, it is preferable that the cells are prepared with use of a specific pathogen free (SPF) fertile egg embryo.

A chicken fertile egg for use in the establishment of the chicken ES cells according to the present invention is not particularly limited, as far as it is freshly laid one and as fresh as possible. In order to determine, from the feather color, whether or not the established cell has the pluripotency, it is preferable that a breed having black feather (e.g., Barred Plymouth Rock) is used. Note that the feather color is one of indicators, and the present invention is not particularly limited in terms of chicken breeds, since there is a case where the one determined not to be a feather color chimera is a germ line chimera.

It is preferable that a blastoderm collected from the chicken fertile egg is at stage X according to the normal development stage table described in "Eyal-Giladi H. & Kochav S., From cleavage to primitive streak formation: a complementary normal table and a new look at the first stages of the development of the chick. I. General morphology. Dev Biol. 49(2): 321-37 (1976)", and a blastoderm developed too much should be excluded. It is preferable that the blastoderm is collected by means of ring collection. However, the present invention is not limited to this. The collected cells are dispersed, spread on the supporting cells, and cultured until colonies thereof are formed (for 2 to 3 days after the start of the culture). It is preferable that each of the colonies thus formed is in a range of 50 to 1000 μm in diameter, more preferably in a range of 100 to 500 μm in diameter, and further preferably in a range of 200 to 500 μm in diameter. Note that, it is preferable that the cells (the colonies) at this stage are passaged. For another 2 to 3 days, passage is carried out so that the colonies having the foregoing diameter are formed.

Through this procedure, it is possible to establish chicken ES cells according to the present invention. Further, chicken ES cells according to the present invention can grow without losing its functions, even if the cells are prepared by thawing its frozen stock.

[2. Method for Evaluation of Chicken Embryonic Stem Cells]

As described above, since chicken embryonic stem (ES) cells according to the present invention stably have the pluripotency and the ability of being differentiated into germ cells, the chicken ES cells according to the present invention are applicable to genetic modification technique. So far, there has been no chicken ES cell stably having the pluripotency and the ability of being differentiated into a germ cell.

A person skilled in the art who read the present specification readily understands that evaluation to determine whether or not chicken ES cells are applicable to genetic modification technique can be made by judging whether or not the chicken ES cells stably have the pluripotency and the ability of being differentiated into germ cells. That is, the present invention further provides a method for evaluation of chicken ES cells.

The method for evaluation of chicken ES cells according to the present invention comprises the step of detecting whether or not the chicken ES cells stably have the pluripotency and the ability of being differentiated into germ cells. With this feature, the present invention can carry out evaluation to determine whether or not the ES cells are available for production of a genetically modified chicken.

In one aspect, the method for evaluation according to the present invention is preferably arranged such that said step of detecting is carried out by detection of stable expression of both of Sachi-1 protein and CVH protein in the chicken ES cell, more specifically, by detection of stable expression of both of (a) a protein having the amino acid sequence shown in SEQ ID NO: 2 and (b) a protein having the amino acid sequence shown in SEQ ID NO: 6 in the chicken ES cell.

The expression of the foregoing proteins may be checked with specific antibodies against the respective proteins. As used herein, the term "antibody" refers to immunoglobulins (IgA, IgD, IgE, IgG, IgM, and Fab fragments, F(ab')$_2$ fragments, and Fc fragments thereof), examples of which encompass, but not limited to, polyclonal antibodies, monoclonal antibodies, single-chain antibodies, anti-ideotype antibodies, and humanized antibodies. That is, the antibodies against Sachi-1 protein, CVH protein, and Chiwi protein only need to be specific antibodies against the respective proteins, and may be polyclonal antibodies or monoclonal antibodies. A person skilled in the art who read the present specification readily figures out the amino acid sequences of these proteins, and therefore he/she can readily prepare recombinant proteins thereof and produce target antibodies by immunizing animals.

Detection of the target proteins with antibodies may be carried out by various techniques known in the field.

In another aspect, in the method for evaluation according to the present invention, said step of detecting may be carried out by detection of stable expression of an mRNA of Sachi-1 and an mRNA of CVH in the chicken ES cell, more specifically, by detection of stable expression of (a') a polynucleotide having a sequence complementary to the base sequence shown in SEQ ID NO: 1 and (b') a polynucleotide having a sequence complementary to the base sequence shown in SEQ ID NO: 5 in the chicken ES cell.

It is preferable that, in the method for evaluation according to the present invention, said step of detecting is carried out by further detection of stable expression of chiwi protein in the chicken ES cell, more specifically, by detection of stable expression of (c) a protein having the amino acid sequence shown in SEQ ID NO: 4 in the chicken ES cell.

Note that, in the method for evaluation according to the present invention, said step of detecting may be carried out by further detection of stable expression of an mRNA of chiwi in the chicken ES cell, more specifically, by detection of stable expression of (c') a polynucleotide having a sequence complementary to the base sequence shown in SEQ ID NO: 3 in the chicken ES cell.

The expression of each of the foregoing mRNAs may be confirmed by means of a technique such as RT-PCR. In order to confirm the expression of the mRNAs, an oligonucleotide (primer) for amplification, designed based on the base sequence shown in SEQ ID NO: 1, 3, or 5, may be used. As used herein, the term "oligonucleotide" refers to several to dozens of nucleotides which are chained together, and is used interchangeably with "polynucleotide". A short oligonucleotide is called dinucleotide or trinucleotide, and a long oligonucleotide is represented by the number of polymerized nucleotides e.g., 30 bases or 100 bases. The oligonucleotide may be produced as a fragment of a longer polynucleotide, or may be chemically synthesized. Note that, in the case where an oligonucleotide is used as a primer, it is preferable that the oligonucleotide has a length of 15 to 40 bases, more preferably 15 to 30 bases, further preferably 20 to 30 bases. The length of the primer can be designed as needed by a person skilled in the art, depending on e.g., the use or the condition thereof.

An oligonucleotide used for detection of a polynucleotide containing a sequence complementary to the base sequence shown in SEQ ID NO: 1, 3, or 5 can be synthesized as a full length of or part of the base sequence shown in SEQ ID NO: 1, 3, or 5. Then, the oligonucleotide obtained is used after being labeled by a radioactive nuclide, an enzyme, biotin, a fluorescence reagent, or the like. Further, such the oligonucleotide may be fused with a polynucleotide encoding a tag label (tag sequence or marker sequence) at the 5' or 3' terminal. Further, polymerase chain reaction (PCR) may be carried out with use of a degenerate primer designed based on the amino acid sequence shown in SEQ ID NO: 2, 4, or 6.

It is preferable that, in the method for evaluation according to the present invention, said step of detecting is carried out at least for 10 days. With this, it is possible to determine whether or not the ES cells stably have pluripotency and an ability of being differentiated into germ cells.

It is known that conventional chicken ES cells lose its pluripotency after long-term serial passage (for 10 days or longer). Based on the judgment of whether or not the foregoing proteins or mRNAs are stably expressed in ES cells, it is possible to know whether or not the ES cells stably have the pluripotency and the ability of being differentiated into germ cells. In other words, by carrying out a process to detect expression of the foregoing proteins or mRNAs for 10 days after the start of the passage of the target cells, it is possible to know whether or not the target cells stably have the pluripotency and the ability of being differentiated into germ cells.

As used herein, what is meant by the wording "a protein is stably expressed" encompasses that "an mRNA is stably expressed", and what is meant by the wording "stable expression of a protein" encompasses that "stable expression of an mRNA".

What is meant by the wording "(carrying out a process to detect) for 10 days" herein is that the detection of the target is carried out at least at a beginning and an end of the time period of 10 days and the detection may not be carried out every day in the time period of 10 days. That is, what is meant by the wording "(carrying out a process to detect) for at least 10 days" is that the detection of the target is carried out at least at a beginning and an end of a predetermined term which is 10 days or longer.

[3. Method for Production of Genetically Modified Chicken and Kit]

In order to produce a genetically modified chicken, chicken embryonic stem (ES) cells should be passaged successfully. A conventional method for culturing chicken ES-like cells causes a big problem in production of a genetically modified chicken. Specifically, in a case where the ES-like cells are cultured by means of any known culturing methods, only the non-passaged ES-like cells maintain its totipotency (i.e., an ability for being differentiated into a germ line (a sperm or an ovum)), and ES-like cells obtained after passage lose its totipotency. This shows that it is impossible to produce a genetically modified chicken through passage of ES-like cells after gene introduction into the ES-like cells.

The present invention provides a kit, utilized for production of a genetically modified chicken, including a chicken LIF protein. The kit according to the present invention may include solely a chicken ES cell stably having the pluripotency and the ability of being differentiated into a germ cell, or may further include another reagent (e.g., a medium, and/or another growth factor) as needed.

In order to produce a genetically modified chicken, such a chicken ES-like cell is necessary that can be passaged at least 4 to 5 times after gene introduction. Further, it is important to prevent differentiation of ES cells during genetic engineering of the ES cells. In this regard, a chicken LIF protein (rchLIF) provides an apparently greater effect than a mouse LIF protein (rmLIF).

In a preferable embodiment, the kit according to the present invention further includes a chicken LIF protein (rchLIF). For the chicken LIF protein, refer to Patent Literatures 1 and 2. Patent Literatures 1 and 2 were filed by the inventors of the present invention, and are incorporated by references to the present specification. The chicken LIF protein used in the present embodiment may be a recombinant produced in a prokaryotic host (i.e., a prokaryotic-type) or a recombinant produced in a eukaryotic host (i.e., a eukaryotic-type), however, the eukaryotic-type is more preferable. In a preferable embodiment, the kit according to the present invention may include a purified protein as a eukaryotic-type of chicken LIF protein or a cell that stably supplies a eukaryotic-type of chicken LIF protein. It is preferable that such the cell is a cell indicated by accession no. [FERM BP-10199] (deposited date: Jan. 5, 2005, deposited with International Patent Organism Depositary (IPOD), National Institute of Advanced Industrial Science and Technology (AIST), Central 6, 1-1-1, Higashi, Tsukuba-shi, Ibaraki-ken, 305-8566 JAPAN). Further, the kit according to the present embodiment may include, as the eukaryotic-type of chicken LIF protein, a conditioned medium obtained by culturing such the cell.

A mature form of rchLIF which is secreted by the foregoing cell has the amino acid sequence shown in SEQ ID NO: 8, which is already cut off a signal peptide of the immature form (i.e., the base sequence encoding the rchLIF is shown in SEQ ID NO: 7). By having a certain sugar chain added, the foregoing eukaryotic-type of chicken LIF protein is physicochemically stable and has a high bioactivity. It is preferable that the eukaryotic-type of chicken LIF protein has, as a sugar chain, a high-mannose type N-linkage, bisecting GlcNAc, sialic acid, or β-linked galactose. It is more preferable that the eukaryotic-type of chicken LIF protein has a sugar chain of a high-mannose type N-linkage, bisecting GlcNAc, and a side chain of sialic acid.

The method for production of a genetically modified chicken according to the present invention is not particularly limited, as far as it uses the foregoing kit. Specifically, the method for production of a genetically modified chicken according to the present invention only needs to comprise the step of culturing the foregoing chicken ES cells together with a chicken LIF protein.

The present invention is not limited to the description of the embodiments above, but may be altered by a skilled person within the scope of the claims. An embodiment based on a proper combination of technical means disclosed in different embodiments is encompassed in the technical scope of the present invention.

Further, all of the academic documents and the patent literatures listed herein are incorporated by references to the present specification.

EXAMPLES

[1. Establishment of Chicken ES Cells]
[1-1. Chicken ES Cell Culturing Medium]

ES cells were cultured and passaged by using a medium (Chicken Embryonic Stem cell Medium (CESM)) having the following composition:

| | |
|---|---|
| EmbryoMax DMEM (Chemicon) | 764 mL |
| Knockout serum replacement (KSR, Gibco) | 200 mL |
| Chicken serum (Gibco) | 20 mL |
| 100 mM sodium pyruvate solution (Wako) | 1 mL |
| MEM non-essential amino acid (Gibco) | 5 mL |
| Nucleoside stock solution | 10 mL |
| (Total) | 1000 mL |

The nucleoside stock solution used was prepared by dissolving 80 mg of adenosine, 85 mg of guanosine, 73 mg of cytidine, 24 mg of thymidine, and 73 mg of uridine (all reagents are manufactured by Sigma) in 100 ml of distilled water, and performing filter sterilization of the solution obtained. Further, just before CESM was used, a β-mercaptorthanol diluted solution was added to CESM at a concentration of 1 μL/mL (i.e., 7 μL of β-mercaptorthanol was added to 1 mL of the CESM). At the same time, a natural chicken LIF protein was added to CESM at a concentration of 20 ng/mL. The natural chicken LIF protein was obtained by purifying a protein produced by introduction of a chicken LIF gene into a chicken embryonic fibroblast line (OU2) indicated by accession no. [FERM BP-10199] (see Patent Literature 2).

[1-2. Supporting Cell]

CEF cells or STO cells were cultured in 10% FBS-DMEM until they became confluent. The CEF cells used were prepared from embryos obtained from SPF fertile eggs incubated for 10 days, according to a known procedure. The STO cells were supplied from the American Type Culture Collection (ATCC).

For the cells which had become confluent, 1 mg/mL of mitomycine C-PBS was added to the medium (final concentration: 10 µg/mL). After being cultured for two hours, the cells were washed with PBS three times. Then, the medium was replaced with a fresh medium. After that, the cells were cultured for several hours to overnight.

200 µL of 0.1% gelatin (Sigma: Type A, G-2625)-DW which had been dissolved and sterilized by an autoclave was added to a 24 well plate in advance, and was left at rest for an hour. The cells cultured as described above were washed with PBS three times. Then, the cells were collected by trypsinization, and counted.

The cells were suspended in 10% FBS-DMEM at $1 \times 10^5$ cells/mL, and the cells suspended were spread to the 24 well plate at $4 \times 10^4$ cells/well ($2 \times 10^4$ cells/cm$^2$). The cells are available as supporting cells after all of the cells are adhered to the wells. (Note that it is preferable that the cells are used within 5 days after the spreading.)

[1-3. Chicken ES Cells]

Stage X blastoderms were collected by means of ring collection. The area pellucida was collected therefrom and floated in a tube into which 1 mL of LIF-added CESM was added, and the cells were dispersed by pipetting. The medium was removed from the foregoing supporting cells, and the cells dispersed were added to the supporting cells. The cells were cultured in an atmosphere of 3% $O_2$ and 5% $CO_2$ at 37° C. by an incubator. The blastodermal cells cultured formed circular colonies of 100 to 500 µm (in diameter) after 2 to 3 days. FIG. 1 shows the morphology of the colonies of the blastodermal cells observed after 3 days in culture. The colonies were collected, and cultured for 3 to 5 days on the supporting cells in a 6 well plate (or 35 mm culture dish) which had been cultured according to the foregoing method. Half of the medium was replaced every day. A colony grown to 200 to 500 µm (in diameter) was passaged in a similar manner. Thereafter, the colony was passaged in a similar manner at 2 day- to 3 day-intervals. FIG. 2 shows the chicken ES cells stably growing even after being passaged. (b) of FIG. 2 is a high magnification view of (a) of FIG. 2. In (b) of FIG. 2, a nucleus and a prominent nucleolus in the cytoplasm are observed.

[1-4. Freeze Storage of Chicken ES Cells]

The colony of the ES cells obtained after 2 days in passage using a 6 cm culture dish was collected and floated again in 1 mL of a solution for freeze storage of cells (CELLBANKER 1; Juji Field Inc.). Then, 1 mL of the solution for freeze storage of cells in which solution the cells were floated was added to a 1.5 mL tube for freeze storage of cells, which tube was then put into a container for freeze storage of cells (NALGENE Cryo 1° C.) and preserved in a −85° C. deep freezer (if necessary, liquid nitrogen or −150° C. freezer may be used).

A medium which had been warmed up was added thereto, so that the frozen cells were thawed quickly. After thawed, the cells were washed by being subjected to centrifugation with use of the ES cell culturing medium which had been warmed up to 37° C. Then, the cells were cultured according to the procedure same as that of the passage. Note that the medium and the like were warmed up to 37° C. before they were used in the culture.

FIG. 3 shows the established chicken ES cells (2 lines) which were prepared by thawing its frozen stock. This shows that the cells of either line showed the same colonial morphology as observed immediately after its establishment ((a) shows the cells observed over one year after its establishment; (b) shows the cells observed over half a year after its establishment).

[2. Marker of Chicken ES Cells]

[2-1. Molecule Sachi-1 Contributing to Chicken ES Cell's Maintaining Pluripotency]

[I] cDNA Cloning of Sachi-1

A conventional method for judging whether or not cells are ES cells is carried out by detection of SSEA-1 with use of an antibody or by detection of alkaline phosphatase activity. In recent years, in mouse ES cells and primate ES cells, some molecules related to ES cell's maintaining its pluripotency have been found. For example, it has been reported that Nanog found in mouse ES cells is essential for ES cells to maintain its pluripotency in vitro (see Non-Patent Literatures 6 and 7). Expression of such a gene or protein is utilized as a new marker of ES cell's maintaining its pluripotency. However, in chickens, an effective marker like this has not been found.

The inventors of the present invention found, with our unique point of view and analysis, a gene useful for evaluation of chicken ES cells. Specifically, focusing on the fact that a human Nanog gene and a mouse Nanog gene were encoded in proximity to von Willebrand factors on human chromosome 12 and mouse chromosome 6, respectively, the inventors of the present invention found, from the genome sequence of chicken chromosome 1 in which a von Willebrand factor was encoded, some gene fragments having homology with mammal Nanog genes. Based on the sequences of these gene fragments, the inventors of the present invention determined a whole mRNA sequence of a Nanog-like homologue (Sachi-1).

A cloned Sachi-1 mRNA has a full length of 3130 by (estimated CDS: 930 bp) (SEQ ID NO: 1), and encodes 309 amino acids (SEQ ID NO: 2). From an estimated amino acid sequence thereof, tryptophan (W) repeat, existing at the C-terminal of the homeodomain and being regarded as a feature of mammal Nanog, was not found in Sachi-1 (see the arrows in (a) of FIG. 4). Further, an identity between Sachi-1 and Nanog was worked out, and the result showed that Sachi-1 was merely 24.3% identical with human Nanog and merely 24.6% identical with mouse Nanog. Furthermore, except for the homeodomain highly-conserved between human Nanog and mouse Nanog (see the box in (a) of FIG. 4), Sachi-1 was hardly conserved.

However, focusing on the homeodomain only, Sachi-1 was 65% identical with human Nanog and 65% identical with mouse Nanog (see (b) of FIG. 4). A phylogenetic tree, created based on the amino acid sequences of homeoproteins obtained through Blastp search, showed that Sachi-1 was most closely related to human Nanog and mouse Nanog, and comparison using a phylogenetic tree, created based on the homeodomain only, also showed that Sachi-1 was most closely related human Nanog and mouse Nanog (not illustrated).

[II] Gene Expression of Sachi-1 mRNA

In order to determine whether or not Sachi-1 was applicable as a pluripotency marker for ES cells as mouse Nanog and human Nanog were, quantitative expression analysis of a Sachi-1 mRNA was carried out by real-time PCR. The base sequence of a primer used to confirm if the Sachi-1 mRNA had been expressed was 5'-ATGACAGCTTGCAGGCAGAAG-3' (SEQ ID NO: 9) for the forward primer, and 5'-CG- TACAGGAGAGCTCGAGAACTG-3' (SEQ ID NO: 10) for the reverse primer. The result showed that a highest expression rate of Sachi-1 mRNA was observed in the blastodermal cells, which were obtained from freshly laid eggs and from which chicken ES cells are to be prepared. A second highest expression rate of Sachi-1 mRNA was observed in the primordial germ cells. The result also showed that a small amount of Sachi-1 mRNA was expressed in an ovary, however, the Sachi-1 mRNA was not expressed in any other somatic cells at all (see FIG. 5). These results show that the Sachi-1 mRNA is transcribed only in cells having the pluripotency or in germ line cells.

[2-2. Molecule Chiwi Expressed in Germ Line Cell]

[I] cDNA Cloning of Chiwi

It is known that a Piwi gene, cloned from the germ line cell of Drosophila, is a gene specifically expressed in the germ line cell in Drosophila. The major functions of the Piwi gene are still unknown. However, a human gene and a mouse gene homologue of the Piwi gene (Hiwi for a human, Miwi for a mouse) were cloned successively, and it is known that such the genes are genes specifically expressed in the germ line cells, as well as the Piwi gene of Drosophila. The inventors of the present invention found that a Piwi homologous gene existed in a chicken, and cloned the Piwi homologous gene for the first time.

It was found that a cloned chiwi cDNA (3363 bp, SEQ ID NO: 3) encoded 867 amino acids (SEQ ID NO: 4) and was 65% identical with Piwi, and 77% identical with Hiwi and Miwi at the amino acid level. Furthermore, a phylogenetic tree, created based on the amino acid sequences of Piwi family, showed that chiwi was most closely related to Hiwi and Miwi (not illustrated). Here, Table 1 shows an identity and a similarity between chiwi and Piwi family molecules at the amino acid level.

TABLE 1

| | Piwi | Hiwi | Miwi | Seawi | Hili | Mili |
|---|---|---|---|---|---|---|
| Chiwi identity (%) | 65.1 | 77.4 | 77.4 | 46.5 | 38.9 | 39.4 |
| Chiwi similarity (%) | 90.9 | 96.0 | 95.9 | 82.5 | 78.8 | 81.7 |

[II] Gene Expression of Chiwi mRNA

In order to determine whether or not chiwi mRNA was specifically expressed in a germ line cell, expression analysis on various tissues and cells of chickens was carried out by real-time PCR. The base sequence of a primer used to confirm if chiwi mRNA had been expressed was 5'-CCAGGATTCA-CAAGTTCTATTC-3' (SEQ ID NO: 11) for the forward primer, and 5'-GCACAGGCATCTCTAAATCTTC-3' (SEQ ID NO: 12) for the reverse primer. The result showed that a highest expression rate of chiwi mRNA was observed in the testis, and a second highest expression rate thereof was observed in the primordial germ cells (PGCs), a third highest expression rate thereof was observed in the blastodermal cells, and a fourth highest expression rate thereof was observed in the ovary. This shows that chiwi is a gene specifically expressed in germ line cells, as well as Piwi, Hiwi, and Miwi (FIG. 6).

[3. Evaluation of Ability of Being Differentiated into Germ Cells]

[3-1. Evaluation of ES Cells Using Antibody]

A Vasa homologue (CVH, SEQ ID NO: 5 and 6), which is expressed in a germ line cell, is already known. The inventors of the present invention produced respective recombinant proteins of Sachi-1, chiwi, and CVH. Specifically, a protein having a full length of the amino acid sequence shown in SEQ ID NO: 2 was constructed for Sachi-1; a protein having the 246- to 504-positions (SEQ ID NO: 15) of the amino acid sequence shown in SEQ ID NO: 4 was constructed for chiwi; a protein having the 116- to 464-positions (SEQ ID NP: 16) of the amino acid sequence shown in SEQ ID NO: 6 was constructed for CVH. These proteins were used to immunize rabbits, so that respective polyclonal antibodies against them were produced. The polyclonal antibodies were purified with use of antigen-bound column to give specific antibodies only. Further, the respective recombinant proteins were used to immunize mice, and specific antibody-producing hybridoma was established by means of cell fuse technique, so that monoclonal antibodies specifically recognizing the respective proteins were produced.

These antibodies were analyzed in their specificities. Firstly, fluorescence antibody technique was carried out on blastodermal cells (the area pellucida of the blastoderm) maintaining the pluripotency and retaining the ability of being differentiated into germ cells (FIG. 7). (a) of FIG. 7 shows a transmission image of the cells; (b) shows an image of the cell immunostained with anti-Sachi-1 antibody; (c) of FIG. 7 shows an image of the cells immunostained with anti-CVH antibody. As illustrated, all of the blastodermal cells were Sachi-1 positive cells (expression was observed in each nucleus), and among these a small number of CVH positive cells were found. The CVH positive cells are also Sachi-1 positive cells, and are differentiated into primordial germ cells (PGCs) or germ cells. This result accords to the previously reported result. That is, ES cells must be established in such a manner that the ES cells include CVH positive cells, and the CVH positive cells must not be lost in the process of establishment of ES cells.

Further, the result of the fluorescence antibody technique carried out on blastodermal cells (the area pellucida of the blastoderm) showed that chiwi positive cells were also found in the cells of the area pellucida of the blastoderm (FIG. 8). (a) of FIG. 8 shows a transmission image of the cells; (b) of FIG. 8 shows an image of the cells stained with DAPI; (c) of FIG. 8 shows an image of the cells immunostained with anti-chiwi antibody. The DAPI stains the nuclei of all of the cells. Considering this, it is understood that, unlike the CVH positive cell, the chiwi positive cell is observed in not all of the blastodermal cells.

Figure 9:
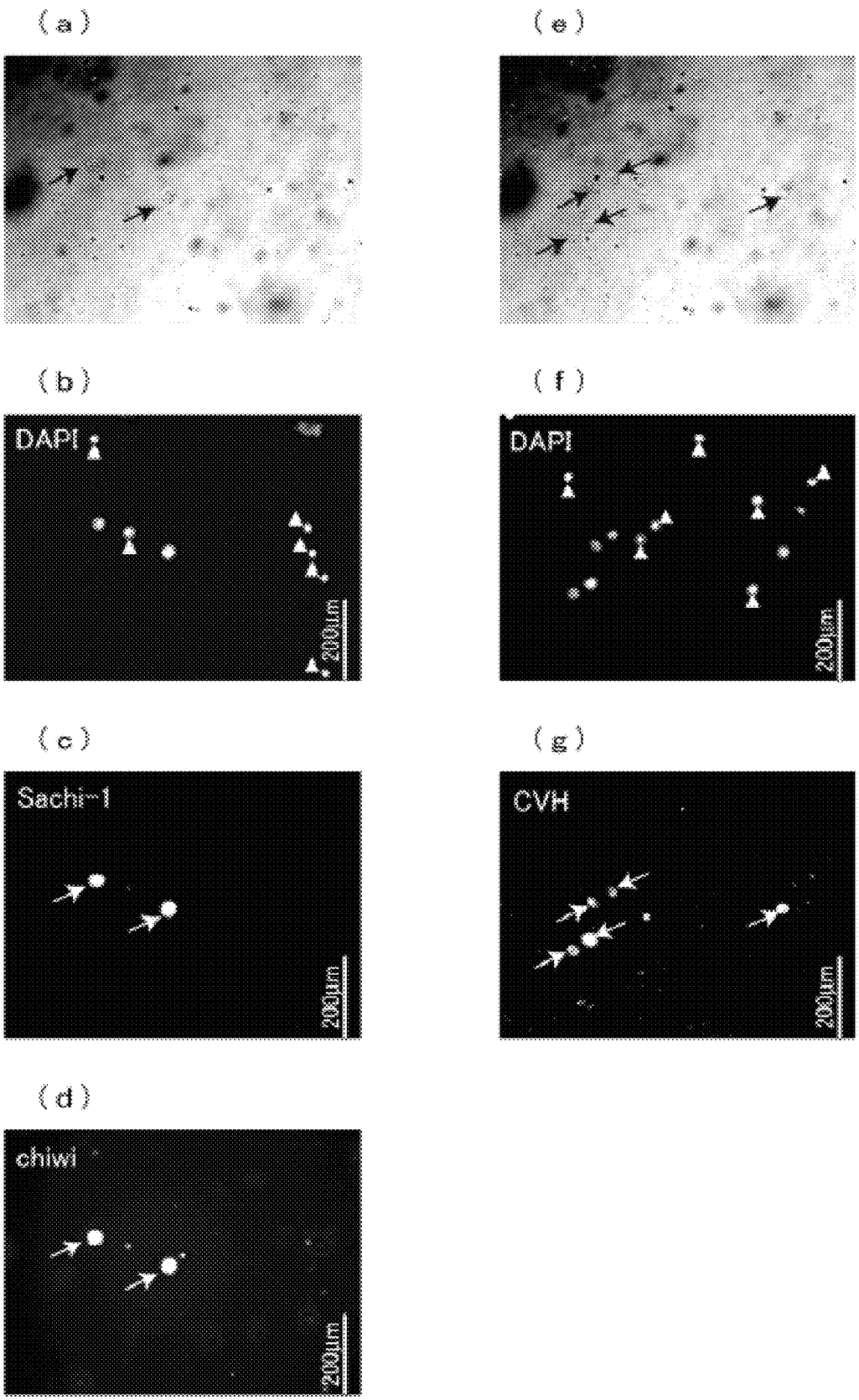
FIG. 9

Similarly, primordial germ cells (PGCs) were evaluated by means of the fluorescence antibody technique. As a result, it was found that the PGCs were positive for all of Sachi-1, CVH, and chiwi (FIG. 9). Each of (a) and (e) of FIG. 9 shows a transmission image of the cells; each of (b) and (f) of FIG. 9 shows an image of the cells stained with DAPI; (c) of FIG. 9 shows an image of the cells immunostained with anti-Sachi-1 antibody; (d) of FIG. 9 shows an image of the cells immunostained with anti-chiwi antibody; and (g) of FIG. 9 shows an image of the cells immunostained with anti-CVH antibody. The results of (a) to (d) of FIG. 9 were obtained by observation of the same view field, and the results of (e) to (g) of FIG. 9 were obtained by observation of the same view field. The arrows in FIG. 9 show the cells positive for the respective antibodies. Since the sample used was cPGCs circulating in the blood stream, erythrocytes were got mixed in addition to the PGCs (the arrowheads in FIG. 9).

FIG. 10 shows a result of evaluation carried out on a testis section. The result showed that a Sachi-1 positive cell was not detected (not illustrated), but CVH positive cells (a) and chiwi positive cells (b) were observed. The upper views of FIG. 10 are the ones observed with a low magnification, and the lower views of FIG. 10 are the ones observed with a high magnification. In both of the views of the low magnification and the views of the high magnification, the black regions represent "positive". CVH was found in the male germ cells before meiosis by which spermatogonia develop to spermatocytes, but was not found in the sperm cells or the sperms. On the other hand, chiwi was found in the germ cells except for the sperm cells.

Figure 11:
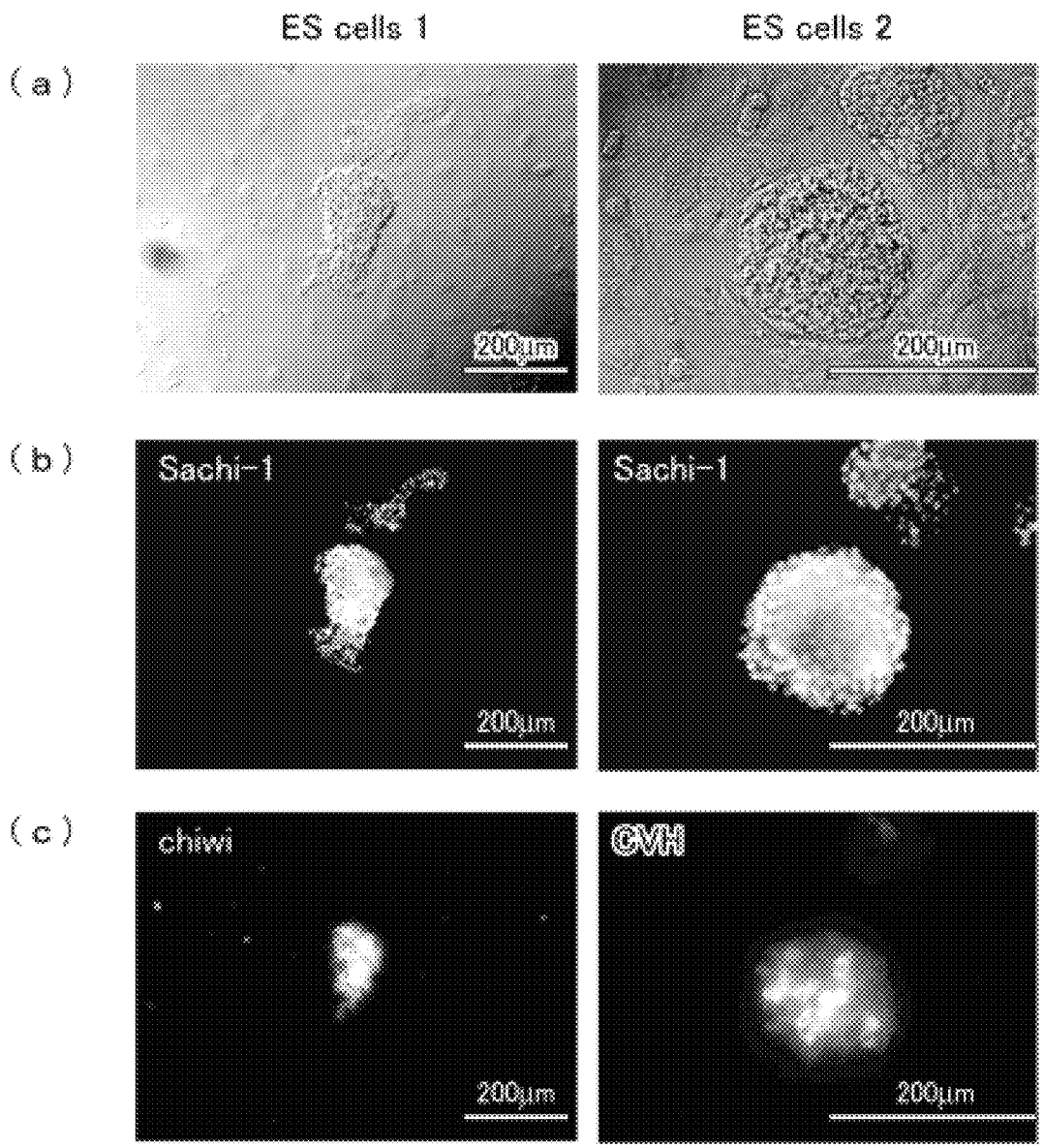
FIG. 11

Not all of the cells having the pluripotency have the ability of being differentiated into germ cells. However, by evaluating in vitro expression of the proteins by means of the immunostaining using the foregoing specific antibodies, it is possible to easily determine if chicken ES cells have the pluripotency and retain the ability of being differentiated into germ cells. Over half of the chicken ES cells established with the present invention have both of the pluripotency and the ability of being differentiated into germ cells. FIG. 11 shows results of the fluorescence antibody technique carried out on, out of the established chicken ES cells, chicken ES cells of two different lines. (a) of FIG. 11 shows transmission images of the cells; (b) of FIG. 11 shows images of the cells immunostained with anti-Sachi-1 antibody; (c) of FIG. 11 shows images of the cells immunostained with anti-chiwi antibody. As described above, it is essential for chicken ES cells available for production of a genetically modified chicken to be strongly positive for anti-Sachi-1 antibody (in the nucleus only) and be strongly positive for anti-CVH antibody (in the cytoplasm only). In order to further increase the reliability of the evaluation, it is more preferable that such the chicken ES cells are weakly positive for anti-chiwi antibody (in the whole of the cells).

[3-2. Evaluation of ES Cells According to Gene Expression]

In order to carry out evaluation to determine, according to in vitro gene expression level, whether or not chicken ES cells have the pluripotency and retain the ability of being differentiated into germ cells, it is necessary that both of the mRNA of Sachi-1 and the mRNA of CVH are expressed in the chicken ES cells. Further, in order to further increase the reliability of the evaluation, it is more preferable that the mRNA of Chiwi is also expressed in the chicken ES cells. This evaluation can be easily made by RT-PCR or real-time PCR. The base sequence of a primer used to confirm if the CVH mRNA had been expressed was 5'-CGTGGCAGCCCTTTTGC-3' (SEQ ID NO: 13) for the forward primer, and 5'-TTCAGAGCGTC-CTTTGAGAACTC-3' (SEQ ID NO: 14) for the reverse primer. FIG. 12 shows a result of gene expression studied in established chicken ES cells. The established ES cells 1 and 2 exhibit gene expression modes similar to that of blastodermal cells having the pluripotency and the ability of being differentiated into germ cells. However, of the established ES cells, the one which lacks expression of a gene, as the cell 3, was found. Thus, the use of Sachi-1, chiwi, and CVH makes it possible to easily evaluate the characteristics of established chicken ES cells, according to gene expression thereof.

[4. Chicken ES Cells Available for Genetic Modification Technique]

Chicken ES cells available for production of a genetically modified chicken must satisfy the followings: (1) The chicken ES cells should be able to be passaged for a long term in a natural state; (2) The chicken ES cells should form colonies, and, as well as mouse ES cells and primate ES cells, the chicken ES cells should have a nucleus occupying a large area relative to the cytoplasm and retain a prominent nucleolus. Further, such the chicken ES cells established must satisfy the followings: (3) Such the chicken ES cells established should maintain its pluripotency and its ability of being differentiated into germ cells, even in a case such the chicken ES cells, prepared by thawing its frozen stock, is cultured again; (4) Such the chicken ES cells established should maintain, even after being genetically modified, its pluripotency and its ability of being differentiated into germ cells.

In view of the foregoing results, it has been concluded that preferable conditions for obtaining chicken ES cells satisfying those conditions are as follows: (I) Cells at up to chicken embryonic developmental stage X should be used; (II) In case of using blastodermal cells (at stage X), only the cells of the area pellucida including precursor cells of the germ cells should be used; (III) The biochemical, gene expression-related characteristics of chicken ES cells are irrelevant to expression of SSEA-1 or the presence or absence of alkaline phosphatase activity, which were conventionally reported to be relevant. Instead of these, both of the mRNA of Sachi-1 and the mRNA of CVH should be expressed in the chicken ES cells (preferably, the mRNA of chiwi is also expressed in the cells), or products (proteins) of genes thereof should be detected in predetermined intracellular organs of the chicken ES cells.

Thus, it is possible to obtain chicken ES cells stably having the pluripotency and the ability of being differentiated into germ cells, and it is possible to apply the chicken ES cells obtained to technique for a genetically modified chicken. Further, with the present invention, it is possible to carry out evaluation to determine whether or not the cell is applicable to the technique for a genetically modified chicken.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

It was determined whether or not established chicken ES cells maintained, even after gene introduction, its pluripotency and its ability of being differentiated into germ cells. EGFP was introduced into the established chicken ES cells, and the cells were treated with 0.025% trypsin and 1 mM EGTA-PBS at 37° C. for 5 minutes, so that colonies thereof were dispersed into single cells. To the above-mentioned chicken ES cell culturing medium, Y-27632 (ROCK (Rho-associated coiled-coil forming kinase/Rho-associated kinase) inhibitor) was added at a final concentration of 10 mM. The ES cells dispersed into the single cells were suspended in the culturing medium at 50 cells/10 mL. The suspended cells were spread to a 96 well plate in which supporting cells (STO) were cultured in advance, in such a manner that 100 mL of the suspended cells were spread to each well. This led to 0.5 cell/well theoretically, thereby surely obtaining at least one well which possesses a single cell. The medium was replaced with a new one so that culture was carried out continuously, and a colony which was solely formed in one well was selected. The passage was carried out in accordance with the foregoing procedure. The cells stably grown were stained with anti-CVH antibody, and a colony in which EGFP was expressed and a colony in which CVH was expressed were selected.

The fact that the chicken ES cells could be dispersed into the single cells even after the gene introduction means that cell lines are obtained from such the chicken ES cells. Further, as illustrated in (a) and (b) of FIG. 13, such chicken ES cells could be obtained that exhibited, in the whole of the colony thereof, expression of EGFP which had been introduced into the chicken ES cells. Furthermore, as illustrated in (c) of FIG. 13, most of these chicken ES cells were CVH positive cells i.e., cells having the ability for being differentiated into germ cells. These results show that the technique according to the present invention not only produces germ line chimeric chickens at a high rate, but also is applicable to high-level genetic modification technique (knock-in/knock-out).

The above-mentioned chicken ES cell line (the cells into which EGFP had been introduced and positive for CVH) was interplanted into a recipient embryo. After the recipient embryo was incubated for 2 to 3 days, embryonic blood was collected therefrom. Although primordial germ cells (PGCs) are temporarily circulating in the embryonic blood at this stage, it is possible to easily distinguish the primordial germ cells from erythrocytes in a bright field of an optical microscope, since the two are different in shape. The PGCs derived from the ES cell line can be distinguished from the PGCs derived from the recipient embryo, depending on the presence or absence of EGFP.

As indicated by the arrows in FIG. 14, the PCG had many granules in its cell, and was observed with a microscope as being a cell larger than an embryonic erythrocyte (see the left views of (a) and (b) of FIG. 14). Observation of this view field with a fluorescence microscope showed that the PGC existing in this view field was positive for EGFP and was derived from the EGFP-introduced ES cell line, which was interplanted and positive for CVH (see the right views of (a) and (b) of FIG. 14). This result shows that it is possible to determine at an early stage that a produced ES cell line is differentiated into germ cells, and also shows that a produced ES cell line is surely differentiated into germ cells.

Similarly, the chicken ES cell lines (into which EGFP had been introduced and which was positive for CVH) were interplanted into recipient embryos. After incubation, chimeras (10 or more day-old-embryos, partially hatched chicks) were obtained, and the gonads were collected therefrom. Genomic DNAs (30 samples) were prepared from the gonads thus collected, and then PCR was carried out by using the genomic DNAs as templates, for detection of EGFP. The base sequence of a primer used was 5'-gtaaacggccacaagttcag-3' (EGFP-SF, SEQ ID NO: 17) for the forward primer, and 5'-cttgtacagctcgtccatgc-3' (EGFP-SR, SEQ ID NO: 18) for the reverse primer. A result of the PCR is shown in FIG. 15.

In FIG. 15, "M" represents a marker; "1" represents a positive control in which PCR was carried out by using an EGFP gene as a template; "2" represents a negative control in which PCR was carried out without any templates; "3" to "32" represent the respective results of PCR carried out by using, as templates, the genomic DNAs which were prepared from the gonads extracted.

As illustrated in FIG. 15, EGFP genes were detected in the gonads of 14 samples out of the 30 samples. Thus, it was confirmed that the cells into which EGFP had been introduced and were positive for CVH were differentiated into the gonads with a high rate (approximately 47%).

The chicken ES cells selected in this manner were interplanted into recipient embryos, and the recipients were incubated, so that first generation chimeric chickens were born. FIG. 16 shows views demonstrating that the established and evaluated chicken ES cells contributed to the germ line. (a) of FIG. 16 shows a chick (upper) and a sexually matured individual (lower) of the first generation chimeric chicken (G0) born by interplanting the ES cells. The ES cells interplanted were derived from Barred Plymouth Rock (black feather). Therefore, as illustrated in (a) of FIG. 16, the first generation chimeric chickens can be identified by the black-and-white-mixed feather color. Further, by sexually maturing the first generation chimeric chickens (G0), the second generation chickens (G1) having black feather were stably born with probability of approximately 3%. (b) of FIG. 16 shows a chick (black feather) of the G1 generation born by artificially inseminating the chicken illustrated in (a) of FIG. 16.

As for feather color genes of chickens, white is dominant to black. Therefore, unless ES cells derived from a black-feathered chicken are differentiated into germ cells, a black-feathered chicken cannot be born as G1. For example, in a case where G0 is a male, a sperm of the G0 generation chicken is artificially inseminated to a black-feathered female. In a case where G0 is a female, a sperm of a black-feathered male chicken is artificially inseminated to the female. In either case, unless the ES cells derived from the black-feathered chicken are differentiated into germ cells, a black-feathered chicken cannot be born at G1. In other wards, a person skilled in the art readily understands the following: The black-feathered chicken of the G1 generation born according to the foregoing method is a final proof of the fact that chicken ES cells according to the present invention can be differentiated into germ cells, and demonstrates the fact that the G1 generation individual obtained inherits a gene derived from the ES cells.

Thus, it was demonstrated that chicken ES cells according to the present invention surely has the ability of being differentiated into germ cells, and is suitable for production of a genetically modified chicken. Further, it was demonstrated that a method for evaluation of such chicken ES cells according to the present invention are an excellent evaluation method that contributes to production of a genetically modified chicken.

Industrial Applicability

The present invention established a chicken embryonic stem cell line having an ability of being differentiated into germ cells, so that production of a genetically modified chicken became practical. In other words, by utilizing the present invention, it is possible to easily produce a desired genetically modified chicken. The genetically modified chicken produced can be effectively utilized in various aspects as animal plants.

The invention claimed is:

1. A method of determining a chicken embryonic stem cell that has pluripotency and an ability of being differentiated into a germ cell, the method comprising the step of:

detecting stable expression of a chicken Nanog protein having the amino acid sequence of SEQ ID NO: 2, a chicken Vasa protein having the amino acid sequence of SEQ ID NO: 6, and a chicken piwi protein having the amino acid sequence of SEQ ID NO: 4 in a chicken embryonic stem cell, wherein stable expression of the chicken Nanog protein, the chicken Vasa protein and the chicken piwi protein indicates the chicken embryonic stem cell has pluripotency and an ability of being differentiated into a germ cell.

2. The method as set forth in claim 1, further comprising the step of selecting a chicken embryonic stem cell which stably expresses the chicken Nanog protein, the chicken Vasa protein and the chicken piwi protein.

3. A method of selecting a chicken embryonic stem cell by using the method as set forth in claim 1.

* * * * *